(12) United States Patent
Williams et al.

(10) Patent No.: US 12,268,389 B2
(45) Date of Patent: Apr. 8, 2025

(54) SURGICAL STAPLING DEVICE WITH FIRING LOCKOUT

(71) Applicant: Covidien LP, Mansfield, MA (US)

(72) Inventors: Justin P. Williams, Southbury, CT (US); Christopher W. Kaswer, Avon, CT (US)

(73) Assignee: Covidien LP, Mansfield, MA (US)

( * ) Notice: Subject to any disclaimer, the term of this patent is extended or adjusted under 35 U.S.C. 154(b) by 253 days.

(21) Appl. No.: 17/977,020

(22) Filed: Oct. 31, 2022

(65) Prior Publication Data

US 2023/0149016 A1 May 18, 2023

Related U.S. Application Data

(60) Provisional application No. 63/278,586, filed on Nov. 12, 2021.

(51) Int. Cl.
  *A61B 17/072* (2006.01)
  *A61B 17/28* (2006.01)

(52) U.S. Cl.
  CPC ........ *A61B 17/072* (2013.01); *A61B 17/2833* (2013.01); *A61B 2017/07257* (2013.01); *A61B 2017/07271* (2013.01); *A61B 2017/07278* (2013.01); *A61B 2017/07285* (2013.01)

(58) Field of Classification Search
  CPC ........ A61B 2017/07285; A61B 17/072; A61B 2017/07271
  See application file for complete search history.

(56) References Cited

U.S. PATENT DOCUMENTS

| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |

(Continued)

FOREIGN PATENT DOCUMENTS

| AU | 198654765 | 9/1986 |
| CA | 2773414 A1 | 11/2012 |

(Continued)

OTHER PUBLICATIONS

International Search Report and Written Opinion dated Mar. 30, 2023, issued in corresponding international application No. PCT/IB2022/060724, 19 pages.

*Primary Examiner* — Gloria R Weeks

(57) ABSTRACT

A surgical stapling device includes an anvil section, a cartridge section, a staple cartridge, a clamping lever, and a firing assembly. The staple cartridge is releasably supported on the cartridge section and includes a lockout assembly and a knife assembly. The knife assembly includes a knife bar having a cutting blade for cutting tissue clamped between the anvil and cartridge sections. The lockout assembly includes a lockout member that movable from an unlocked position to a locked position and is positioned to shield the cutting blade in both positions. The lockout member is configured to prevent binding of the lockout member to facilitate movement of the lockout member from the unlocked position to the locked position after the stapling device is fired.

20 Claims, 11 Drawing Sheets

(56) References Cited

U.S. PATENT DOCUMENTS

| | | | |
|---|---|---|---|
| 4,429,695 | A | 2/1984 | Green |
| 4,505,414 | A | 3/1985 | Filipi |
| 4,520,817 | A | 6/1985 | Green |
| 4,589,413 | A | 5/1986 | Malyshev et al. |
| 4,596,351 | A | 6/1986 | Fedotov et al. |
| 4,602,634 | A | 7/1986 | Barkley |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,861 | A * | 1/1987 | Chow ............ A61B 17/07207 227/19 |
| 4,633,874 | A | 1/1987 | Chow et al. |
| 4,671,445 | A | 6/1987 | Barker et al. |
| 4,700,703 | A | 10/1987 | Resnick et al. |
| 4,703,887 | A | 11/1987 | Clanton et al. |
| 4,728,020 | A | 3/1988 | Green et al. |
| 4,752,024 | A | 6/1988 | Green et al. |
| 4,784,137 | A | 11/1988 | Kulik et al. |
| 4,863,088 | A | 9/1989 | Redmond et al. |
| 4,869,415 | A | 9/1989 | Fox |
| 4,892,244 | A | 1/1990 | Fox et al. |
| 4,955,959 | A | 9/1990 | Tompkins et al. |
| 4,978,049 | A | 12/1990 | Green |
| 4,991,764 | A | 2/1991 | Mericle |
| 5,014,899 | A | 5/1991 | Presty et al. |
| 5,031,814 | A | 7/1991 | Tompkins et al. |
| 5,040,715 | A | 8/1991 | Green et al. |
| 5,065,929 | A | 11/1991 | Schulze et al. |
| 5,071,430 | A | 12/1991 | de Salis et al. |
| 5,074,454 | A | 12/1991 | Peters |
| 5,083,695 | A | 1/1992 | Foslien et al. |
| 5,084,057 | A | 1/1992 | Green et al. |
| 5,106,008 | A | 4/1992 | Tompkins et al. |
| 5,111,987 | A | 5/1992 | Moeinzadeh et al. |
| 5,129,570 | A | 7/1992 | Schulze et al. |
| 5,141,144 | A | 8/1992 | Foslien et al. |
| 5,156,315 | A | 10/1992 | Green et al. |
| 5,156,614 | A | 10/1992 | Green et al. |
| 5,163,943 | A | 11/1992 | Mohiuddin et al. |
| 5,170,925 | A | 12/1992 | Madden et al. |
| 5,171,247 | A | 12/1992 | Hughett et al. |
| 5,173,133 | A | 12/1992 | Morin et al. |
| 5,180,092 | A | 1/1993 | Crainich |
| 5,188,274 | A | 2/1993 | Moeinzadeh et al. |
| 5,220,928 | A | 6/1993 | Oddsen et al. |
| 5,221,036 | A | 6/1993 | Takase |
| 5,242,457 | A | 9/1993 | Akopov et al. |
| 5,246,156 | A | 9/1993 | Rothfuss et al. |
| 5,253,793 | A | 10/1993 | Green et al. |
| 5,263,629 | A | 11/1993 | Trumbull et al. |
| RE34,519 | E | 1/1994 | Fox et al. |
| 5,275,323 | A | 1/1994 | Schulze et al. |
| 5,282,807 | A | 2/1994 | Knoepfler |
| 5,289,963 | A | 3/1994 | McGarry et al. |
| 5,307,976 | A | 5/1994 | Olson et al. |
| 5,308,576 | A | 5/1994 | Green et al. |
| 5,312,023 | A * | 5/1994 | Green ............ A61B 17/07207 227/19 |
| 5,318,221 | A | 6/1994 | Green et al. |
| 5,326,013 | A | 7/1994 | Green et al. |
| 5,328,077 | A | 7/1994 | Lou |
| 5,330,486 | A | 7/1994 | Wilk |
| 5,332,142 | A | 7/1994 | Robinson et al. |
| 5,336,232 | A | 8/1994 | Green et al. |
| 5,344,061 | A | 9/1994 | Crainich |
| 5,352,238 | A | 10/1994 | Green et al. |
| 5,356,064 | A | 10/1994 | Green et al. |
| 5,358,506 | A | 10/1994 | Green et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,376,095 | A | 12/1994 | Ortiz |
| 5,379,933 | A | 1/1995 | Green et al. |
| 5,381,943 | A | 1/1995 | Allen et al. |
| 5,382,255 | A | 1/1995 | Castro et al. |
| 5,383,880 | A | 1/1995 | Hooven |
| 5,389,098 | A | 2/1995 | Tsuruta et al. |
| 5,395,033 | A | 3/1995 | Byrne et al. |
| 5,395,034 | A | 3/1995 | Allen et al. |
| 5,397,046 | A | 3/1995 | Savage et al. |
| 5,397,324 | A | 3/1995 | Carroll et al. |
| 5,403,312 | A | 4/1995 | Yates et al. |
| 5,405,072 | A | 4/1995 | Zlock et al. |
| 5,407,293 | A | 4/1995 | Crainich |
| 5,413,268 | A | 5/1995 | Green et al. |
| 5,415,334 | A | 5/1995 | Williamson et al. |
| 5,415,335 | A | 5/1995 | Knodell, Jr. |
| 5,417,361 | A | 5/1995 | Williamson, IV |
| 5,423,471 | A | 6/1995 | Mastri et al. |
| 5,425,745 | A | 6/1995 | Green et al. |
| 5,431,322 | A | 7/1995 | Green et al. |
| 5,431,323 | A | 7/1995 | Smith et al. |
| 5,433,721 | A | 7/1995 | Hooven et al. |
| 5,441,193 | A | 8/1995 | Gravener |
| 5,445,304 | A | 8/1995 | Plyley et al. |
| 5,447,265 | A | 9/1995 | Vidal et al. |
| 5,452,837 | A | 9/1995 | Williamson, IV et al. |
| 5,456,401 | A | 10/1995 | Green et al. |
| 5,464,300 | A | 11/1995 | Crainich |
| 5,465,895 | A * | 11/1995 | Knodel ............ A61B 17/07207 227/176.1 |
| 5,467,911 | A | 11/1995 | Tsuruta et al. |
| 5,470,007 | A | 11/1995 | Plyley et al. |
| 5,470,010 | A | 11/1995 | Rothfuss et al. |
| 5,472,132 | A | 12/1995 | Savage et al. |
| 5,474,566 | A | 12/1995 | Alesi et al. |
| 5,476,206 | A | 12/1995 | Green et al. |
| 5,478,003 | A | 12/1995 | Green et al. |
| 5,480,089 | A | 1/1996 | Blewett |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,486,185 | A | 1/1996 | Freitas et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,490,856 | A | 2/1996 | Person et al. |
| 5,497,933 | A | 3/1996 | DeFonzo et al. |
| 5,501,689 | A | 3/1996 | Green et al. |
| 5,505,363 | A | 4/1996 | Green et al. |
| 5,507,426 | A | 4/1996 | Young et al. |
| 5,518,163 | A | 5/1996 | Hooven |
| 5,518,164 | A | 5/1996 | Hooven |
| 5,529,235 | A | 6/1996 | Boiarski et al. |
| 5,531,744 | A | 7/1996 | Nardella et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,542,594 | A | 8/1996 | McKean et al. |
| 5,549,628 | A | 8/1996 | Cooper et al. |
| 5,551,622 | A | 9/1996 | Yoon |
| 5,553,765 | A | 9/1996 | Knodel et al. |
| 5,554,164 | A | 9/1996 | Wilson et al. |
| 5,554,169 | A | 9/1996 | Green et al. |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,701 | A | 10/1996 | Huitema et al. |
| 5,564,615 | A | 10/1996 | Bishop et al. |
| 5,571,116 | A | 11/1996 | Bolanos et al. |
| 5,573,169 | A | 11/1996 | Green et al. |
| 5,573,543 | A | 11/1996 | Akopov et al. |
| 5,575,799 | A | 11/1996 | Bolanos et al. |
| 5,575,803 | A | 11/1996 | Cooper et al. |
| 5,577,654 | A | 11/1996 | Bishop |
| 5,584,425 | A | 12/1996 | Savage et al. |
| 5,586,711 | A | 12/1996 | Plyley et al. |
| 5,588,580 | A | 12/1996 | Paul et al. |

(56) References Cited

U.S. PATENT DOCUMENTS

| | | |
|---|---|---|
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |

(56) References Cited

U.S. PATENT DOCUMENTS

| | | |
|---|---|---|
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |

(56) References Cited

U.S. PATENT DOCUMENTS

| | | |
|---|---|---|
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |

(56) References Cited

U.S. PATENT DOCUMENTS

| | | |
|---|---|---|
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 * | 6/2011 | Smith ............... A61B 17/07207 227/176.1 |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,405 B2 | 2/2012 | Milliman |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |

(56) References Cited

U.S. PATENT DOCUMENTS

| | | | |
|---|---|---|---|
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,597,311 B2 | 12/2013 | Criscuolo et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |

(56) References Cited

U.S. PATENT DOCUMENTS

| | | |
|---|---|---|
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,533 B2 | 6/2014 | Whitman |
| 8,746,534 B2 | 6/2014 | Farascioni |
| 8,746,535 B2 | 6/2014 | Shelton, IV et al. |
| 8,747,421 B2 | 6/2014 | Balbierz et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 * | 12/2014 | Kostrzewski .... A61B 17/07207 227/176.1 |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,681 B2 | 1/2015 | Kostrzewski |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,960,520 B2 | 2/2015 | McCuen |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,991,677 B2 | 3/2015 | Moore et al. |
| 8,991,678 B2 | 3/2015 | Wellman et al. |
| 8,998,058 B2 | 4/2015 | Moore et al. |
| 8,998,060 B2 | 4/2015 | Bruewer et al. |
| 9,005,230 B2 | 4/2015 | Yates et al. |
| 9,010,606 B2 | 4/2015 | Aranyi et al. |
| 9,010,607 B2 | 4/2015 | Kostrzewski |
| 9,010,610 B2 | 4/2015 | Hodgkinson |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,544 B2 | 4/2015 | Hodgkinson et al. |
| 9,016,545 B2 | 4/2015 | Aranyi et al. |
| 9,016,546 B2 | 4/2015 | Demmy et al. |
| 9,017,371 B2 | 4/2015 | Whitman et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |

(56) References Cited

U.S. PATENT DOCUMENTS

| | | |
|---|---|---|
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |
| 9,204,876 B2 | 12/2015 | Cappola et al. |
| 9,204,877 B2 | 12/2015 | Whitman et al. |
| 9,204,880 B2 | 12/2015 | Baxter, III et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,211 B2 * | 3/2016 | Williams .............. A61B 17/068 |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,771 B2 | 5/2016 | Baxter, III et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,479 B2 | 5/2016 | (Tarinelli) Racenet et al. |
| 9,345,481 B2 | 5/2016 | Hall et al. |
| 9,345,780 B2 | 5/2016 | Manoharan et al. |
| 9,351,726 B2 | 5/2016 | Leimbach |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,402,627 B2 | 8/2016 | Stevenson et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,522,002 B2 | 12/2016 | Chowaniec et al. |
| 9,539,007 B2 | 1/2017 | Dhakad et al. |
| 9,549,735 B2 | 1/2017 | Shelton, IV et al. |
| 9,554,794 B2 | 1/2017 | Baber |
| 9,561,029 B2 | 2/2017 | Scheib et al. |
| 9,561,031 B2 | 2/2017 | Heinrich et al. |
| 9,566,065 B2 | 2/2017 | Knodel |
| 9,572,576 B2 | 2/2017 | Hodgkinson et al. |
| 9,579,101 B2 | 2/2017 | Whitman et al. |
| 9,585,657 B2 | 3/2017 | Shelton, IV et al. |
| 9,585,662 B2 | 3/2017 | Shelton, IV et al. |
| 9,597,077 B2 | 3/2017 | Hodgkinson |
| 9,610,080 B2 | 4/2017 | Whitfield et al. |
| 9,615,825 B2 | 4/2017 | Viola |
| 9,615,826 B2 | 4/2017 | Shelton, IV et al. |
| 9,622,746 B2 | 4/2017 | Simms |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,642,620 B2 | 5/2017 | Baxter, III |
| 9,649,109 B2 | 5/2017 | Ranucci et al. |
| 9,655,613 B2 | 5/2017 | Schaller |
| 9,662,108 B2 | 5/2017 | Williams |
| 9,668,728 B2 | 6/2017 | Williams et al. |
| 9,668,732 B2 | 6/2017 | Patel et al. |
| 9,675,351 B2 | 6/2017 | Hodgkinson et al. |
| 9,681,870 B2 | 6/2017 | Baxter, III et al. |
| 9,687,230 B2 | 6/2017 | Leimbach et al. |
| 9,687,233 B2 | 6/2017 | Fernandez et al. |
| 9,693,772 B2 | 7/2017 | Ingmanson et al. |
| 9,700,309 B2 | 7/2017 | Jaworek |
| 9,700,319 B2 | 7/2017 | Motooka et al. |
| 9,706,993 B2 | 7/2017 | Hessler et al. |
| 9,713,474 B2 | 7/2017 | Lorenz |
| 9,717,497 B2 | 8/2017 | Zerkle et al. |
| 9,717,498 B2 * | 8/2017 | Aranyi .............. A61B 17/07207 |
| 9,724,092 B2 | 8/2017 | Baxter, III et al. |
| 9,724,095 B2 * | 8/2017 | Gupta .............. A61B 17/0682 |
| 9,757,126 B2 * | 9/2017 | Cappola .......... A61B 17/07207 |
| 9,763,662 B2 | 9/2017 | Shelton, IV et al. |
| 9,770,245 B2 | 9/2017 | Swayze et al. |
| 9,775,610 B2 | 10/2017 | Nicholas et al. |
| 9,775,635 B2 | 10/2017 | Takei |
| 9,782,169 B2 | 10/2017 | Kimsey |
| 9,782,173 B2 | 10/2017 | Mozdzierz |
| 9,795,379 B2 | 10/2017 | Leimbach et al. |
| 9,795,384 B2 | 10/2017 | Weaner et al. |
| 9,808,246 B2 | 11/2017 | Shelton, IV |
| 9,808,248 B2 | 11/2017 | Hoffman |
| 9,808,249 B2 | 11/2017 | Shelton, IV |
| 9,820,741 B2 | 11/2017 | Kostrzewski |
| 9,820,742 B2 | 11/2017 | Covach et al. |
| 9,827,002 B2 | 11/2017 | Hausen et al. |
| 9,839,420 B2 | 12/2017 | Shelton, IV |
| 9,839,421 B2 | 12/2017 | Zerkle et al. |
| 9,839,428 B2 | 12/2017 | Baxter, III et al. |
| 9,855,038 B2 | 1/2018 | Smith et al. |
| 9,855,040 B2 | 1/2018 | Kostrzewski |
| 9,861,358 B2 | 1/2018 | Marczyk et al. |

(56) References Cited

U.S. PATENT DOCUMENTS

| | | |
|---|---|---|
| 9,861,359 B2 | 1/2018 | Shelton, IV et al. |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,872,683 B2 | 1/2018 | Hopkins |
| 9,883,860 B2 | 2/2018 | Leimbach et al. |
| 9,901,342 B2 | 2/2018 | Shelton, IV et al. |
| 9,913,646 B2 | 3/2018 | Shelton, IV |
| 9,918,714 B2 | 3/2018 | Gibbons, Jr. |
| 9,918,717 B2 | 3/2018 | Czernik |
| 9,924,941 B2 | 3/2018 | Burbank |
| 9,924,942 B2 | 3/2018 | Swayze et al. |
| 9,936,951 B2 | 4/2018 | Hufnagel et al. |
| 9,936,954 B2 | 4/2018 | Shelton, IV et al. |
| 9,943,311 B2 | 4/2018 | Scirica et al. |
| 9,949,737 B2 | 4/2018 | Zergiebel et al. |
| 9,955,966 B2 | 5/2018 | Zergiebel |
| 9,968,354 B2 | 5/2018 | Shelton, IV et al. |
| 9,980,724 B2 | 5/2018 | Farascioni et al. |
| 9,987,012 B2 | 6/2018 | Shah |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,505 B2 | 6/2018 | Moore et al. |
| 10,034,668 B2 | 7/2018 | Ebner |
| 10,039,532 B2 | 8/2018 | Srinivas et al. |
| 10,039,545 B2 | 8/2018 | Sadowski et al. |
| 10,045,782 B2 | 8/2018 | Murthy Aravalli |
| 10,052,044 B2 | 8/2018 | Shelton, IV et al. |
| 10,058,963 B2 | 8/2018 | Shelton, IV et al. |
| 10,064,622 B2 | 9/2018 | Murthy Aravalli |
| 10,076,325 B2 | 9/2018 | Huang et al. |
| 10,085,749 B2 * | 10/2018 | Cappola ............ A61B 17/07207 |
| 10,085,750 B2 | 10/2018 | Zergiebel et al. |
| 10,092,290 B2 | 10/2018 | Yigit et al. |
| 10,092,292 B2 | 10/2018 | Boudreaux et al. |
| 10,111,657 B2 | 10/2018 | McCuen |
| 10,111,665 B2 | 10/2018 | Aranyi |
| 10,117,650 B2 | 11/2018 | Nicholas et al. |
| 10,117,654 B2 | 11/2018 | Ingmanson et al. |
| 10,123,796 B2 | 11/2018 | Westling et al. |
| 10,123,798 B2 | 11/2018 | Baxter, III et al. |
| 10,130,367 B2 * | 11/2018 | Cappola ................ A61B 90/98 |
| 10,135,242 B2 | 11/2018 | Baber et al. |
| 10,143,474 B2 | 12/2018 | Bucciaglia et al. |
| 10,172,612 B2 | 1/2019 | Frushour |
| 10,172,615 B2 | 1/2019 | Marczyk et al. |
| 10,172,617 B2 | 1/2019 | Shelton, IV et al. |
| 10,175,127 B2 | 1/2019 | Collins et al. |
| 10,180,463 B2 | 1/2019 | Beckman et al. |
| 10,182,816 B2 | 1/2019 | Shelton, IV et al. |
| 10,206,677 B2 | 2/2019 | Harris et al. |
| 10,213,201 B2 | 2/2019 | Shelton, IV et al. |
| 10,219,804 B2 | 3/2019 | Linder et al. |
| 10,226,239 B2 | 3/2019 | Nicholas et al. |
| 10,226,250 B2 | 3/2019 | Beckman et al. |
| 10,226,254 B2 | 3/2019 | Cabrera et al. |
| 10,245,033 B2 | 4/2019 | Overmyer et al. |
| 10,245,038 B2 | 4/2019 | Hopkins et al. |
| 10,251,725 B2 | 4/2019 | Valentine et al. |
| 10,265,065 B2 | 4/2019 | Shelton, IV et al. |
| 10,265,066 B2 | 4/2019 | Measamer et al. |
| 10,265,074 B2 | 4/2019 | Shelton, IV et al. |
| 10,271,840 B2 | 4/2019 | Sapre |
| 10,271,841 B2 | 4/2019 | Overmyer et al. |
| 10,285,694 B2 | 5/2019 | Viola et al. |
| 10,285,698 B2 | 5/2019 | Cappola et al. |
| 10,321,907 B2 | 6/2019 | Shelton, IV et al. |
| 10,327,776 B2 | 6/2019 | Harris et al. |
| 10,335,150 B2 | 7/2019 | Shelton, IV |
| 10,349,939 B2 | 7/2019 | Shelton, IV et al. |
| 10,349,941 B2 | 7/2019 | Marczyk et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,405,857 B2 | 9/2019 | Shelton |
| 10,426,468 B2 | 10/2019 | Contini et al. |
| 10,441,279 B2 | 10/2019 | Shelton, IV et al. |
| 10,456,129 B2 | 10/2019 | Shelton, IV et al. |
| 10,456,130 B2 | 10/2019 | Cheney et al. |
| 10,463,368 B2 | 11/2019 | Kostrzewski |
| 10,470,762 B2 | 11/2019 | Leimbach et al. |
| 10,470,911 B2 | 11/2019 | Thompson et al. |
| 10,478,182 B2 | 11/2019 | Taylor |
| 10,478,183 B2 | 11/2019 | Hess et al. |
| 10,478,187 B2 | 11/2019 | Shelton, IV et al. |
| 10,542,976 B2 | 1/2020 | Calderoni et al. |
| 10,548,504 B2 | 2/2020 | Shelton, IV et al. |
| 10,548,593 B2 | 2/2020 | Shelton, IV et al. |
| 10,548,599 B2 | 2/2020 | Marczyk et al. |
| 10,561,417 B2 | 2/2020 | Zergiebel et al. |
| 10,561,418 B2 | 2/2020 | Richard et al. |
| 10,568,621 B2 | 2/2020 | Shelton, IV et al. |
| 10,588,629 B2 | 3/2020 | Malinouskas et al. |
| 10,595,929 B2 | 3/2020 | Boudreaux et al. |
| 10,603,128 B2 | 3/2020 | Zergiebel et al. |
| 10,617,412 B2 | 4/2020 | Shelton, IV et al. |
| 10,624,634 B2 | 4/2020 | Shelton, IV et al. |
| 10,687,806 B2 | 6/2020 | Shelton, IV et al. |
| 10,695,053 B2 | 6/2020 | Hess et al. |
| 10,779,822 B2 | 9/2020 | Yates et al. |
| 10,792,038 B2 | 10/2020 | Becerra et al. |
| 10,828,030 B2 | 11/2020 | Weir et al. |
| 10,863,984 B2 | 12/2020 | Shelton, IV et al. |
| 10,898,187 B2 | 1/2021 | Deck et al. |
| 10,959,729 B2 | 3/2021 | Ehrenfels et al. |
| 11,331,098 B2 * | 5/2022 | Cappola ............ A61B 17/07207 |
| 11,998,215 B2 * | 6/2024 | Foshee ................ A61B 17/122 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084896 A1 * | 4/2007 | Doll ................. A61B 17/07207 227/19 |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2008/0308608 A1 | 12/2008 | Prommersberger |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |

(56) References Cited

U.S. PATENT DOCUMENTS

| | | | |
|---|---|---|---|
| 2010/0065604 A1* | 3/2010 | Weng | A61B 17/07207 227/180.1 |
| 2010/0069942 A1 | 3/2010 | Shelton, IV | |
| 2010/0127041 A1 | 5/2010 | Morgan et al. | |
| 2010/0133317 A1 | 6/2010 | Shelton, IV et al. | |
| 2010/0147921 A1 | 6/2010 | Olson | |
| 2010/0147922 A1 | 6/2010 | Olson | |
| 2010/0155453 A1 | 6/2010 | Bombard et al. | |
| 2010/0193566 A1 | 8/2010 | Scheib et al. | |
| 2010/0224668 A1 | 9/2010 | Fontayne et al. | |
| 2010/0249802 A1 | 9/2010 | May et al. | |
| 2010/0252611 A1 | 10/2010 | Ezzat et al. | |
| 2011/0006101 A1 | 1/2011 | Hall et al. | |
| 2011/0024477 A1 | 2/2011 | Hall | |
| 2011/0024478 A1 | 2/2011 | Shelton, IV | |
| 2011/0036891 A1 | 2/2011 | Zemlok et al. | |
| 2011/0087276 A1 | 4/2011 | Bedi et al. | |
| 2011/0101069 A1 | 5/2011 | Bombard et al. | |
| 2011/0147433 A1 | 6/2011 | Shelton, IV et al. | |
| 2011/0163146 A1 | 7/2011 | Ortiz et al. | |
| 2011/0192882 A1 | 8/2011 | Hess et al. | |
| 2011/0278343 A1 | 11/2011 | Knodel et al. | |
| 2011/0290856 A1 | 12/2011 | Shelton, IV et al. | |
| 2012/0053406 A1 | 3/2012 | Conlon et al. | |
| 2012/0061446 A1 | 3/2012 | Knodel et al. | |
| 2012/0074200 A1 | 3/2012 | Schmid et al. | |
| 2012/0080478 A1 | 4/2012 | Morgan et al. | |
| 2012/0080495 A1 | 4/2012 | Holcomb et al. | |
| 2012/0080498 A1 | 4/2012 | Shelton, IV et al. | |
| 2012/0091183 A1 | 4/2012 | Manoux et al. | |
| 2012/0138659 A1 | 6/2012 | Marczyk et al. | |
| 2012/0193394 A1 | 8/2012 | Holcomb et al. | |
| 2012/0193399 A1 | 8/2012 | Holcomb et al. | |
| 2012/0211542 A1 | 8/2012 | Racenet | |
| 2012/0228358 A1 | 9/2012 | Zemlok et al. | |
| 2012/0234895 A1 | 9/2012 | O'Connor et al. | |
| 2012/0234897 A1 | 9/2012 | Shelton, IV et al. | |
| 2012/0241504 A1 | 9/2012 | Soltz et al. | |
| 2012/0248169 A1 | 10/2012 | Widenhouse et al. | |
| 2012/0286022 A1 | 11/2012 | Olson et al. | |
| 2012/0298722 A1 | 11/2012 | Hess et al. | |
| 2012/0312858 A1* | 12/2012 | Patankar | A61B 17/07207 227/176.1 |
| 2013/0008937 A1 | 1/2013 | Viola | |
| 2013/0012983 A1 | 1/2013 | Kleyman | |
| 2013/0020375 A1 | 1/2013 | Shelton, IV et al. | |
| 2013/0020376 A1 | 1/2013 | Shelton, IV et al. | |
| 2013/0026208 A1 | 1/2013 | Shelton, IV et al. | |
| 2013/0026210 A1 | 1/2013 | Shelton, IV et al. | |
| 2013/0041406 A1 | 2/2013 | Bear et al. | |
| 2013/0068816 A1 | 3/2013 | Mandakolathur Vasudevan et al. | |
| 2013/0068818 A1 | 3/2013 | Kasvikis | |
| 2013/0075447 A1 | 3/2013 | Weisenburgh, II et al. | |
| 2013/0098970 A1 | 4/2013 | Racenet et al. | |
| 2013/0153641 A1 | 6/2013 | Shelton, IV et al. | |
| 2013/0175316 A1 | 7/2013 | Thompson et al. | |
| 2013/0256380 A1 | 10/2013 | Schmid et al. | |
| 2013/0277410 A1 | 10/2013 | Fernandez et al. | |
| 2013/0334280 A1 | 12/2013 | Krehel et al. | |
| 2014/0014704 A1 | 1/2014 | Onukuri et al. | |
| 2014/0014707 A1 | 1/2014 | Onukuri et al. | |
| 2014/0048580 A1 | 2/2014 | Merchant et al. | |
| 2014/0166724 A1 | 6/2014 | Schellin et al. | |
| 2014/0166725 A1 | 6/2014 | Schellin et al. | |
| 2014/0166726 A1 | 6/2014 | Schellin et al. | |
| 2014/0175150 A1 | 6/2014 | Shelton, IV et al. | |
| 2014/0239047 A1 | 8/2014 | Hodgkinson et al. | |
| 2014/0246475 A1 | 9/2014 | Hall et al. | |
| 2014/0252064 A1 | 9/2014 | Mozdzierz et al. | |
| 2014/0263541 A1 | 9/2014 | Leimbach et al. | |
| 2014/0263552 A1 | 9/2014 | Hall et al. | |
| 2014/0263558 A1 | 9/2014 | Hausen et al. | |
| 2014/0284371 A1 | 9/2014 | Morgan et al. | |
| 2014/0291379 A1 | 10/2014 | Schellin et al. | |
| 2014/0291383 A1 | 10/2014 | Spivey et al. | |
| 2014/0367445 A1 | 12/2014 | Ingmanson et al. | |
| 2015/0076211 A1 | 3/2015 | Irka et al. | |
| 2015/0134076 A1 | 5/2015 | Shelton, IV et al. | |
| 2015/0173749 A1 | 6/2015 | Shelton, IV et al. | |
| 2015/0173756 A1 | 6/2015 | Baxter, III et al. | |
| 2015/0250474 A1 | 9/2015 | Abbott et al. | |
| 2015/0272557 A1 | 10/2015 | Overmyer et al. | |
| 2015/0297222 A1 | 10/2015 | Huitema et al. | |
| 2015/0297225 A1 | 10/2015 | Huitema et al. | |
| 2015/0374372 A1 | 12/2015 | Zergiebel et al. | |
| 2016/0066909 A1 | 3/2016 | Baber et al. | |
| 2016/0166249 A1 | 6/2016 | Knodel | |
| 2016/0166253 A1 | 6/2016 | Knodel | |
| 2016/0235494 A1 | 8/2016 | Shelton, IV et al. | |
| 2016/0302791 A1 | 10/2016 | Schmitt | |
| 2016/0354176 A1 | 12/2016 | Schmitt | |
| 2017/0000483 A1 | 1/2017 | Motai et al. | |
| 2017/0112561 A1 | 4/2017 | Motai | |
| 2017/0290584 A1 | 10/2017 | Jasemian et al. | |
| 2017/0296172 A1 | 10/2017 | Harris et al. | |
| 2017/0303924 A1 | 10/2017 | Scheib | |
| 2018/0008260 A1 | 1/2018 | Baxter, III et al. | |
| 2018/0168637 A1 | 6/2018 | Harris | |
| 2018/0168644 A1 | 6/2018 | Shelton, IV et al. | |
| 2018/0235610 A1 | 8/2018 | Harris et al. | |
| 2018/0325514 A1 | 11/2018 | Harris et al. | |
| 2019/0099182 A1 | 4/2019 | Bakos et al. | |
| 2019/0150919 A1 | 5/2019 | Williams et al. | |
| 2019/0261984 A1 | 8/2019 | Nelson et al. | |
| 2019/0298341 A1 | 10/2019 | Shelton, IV et al. | |
| 2019/0314016 A1 | 10/2019 | Huitema et al. | |
| 2019/0314019 A1 | 10/2019 | Rector et al. | |
| 2020/0054323 A1 | 2/2020 | Harris et al. | |
| 2020/0121317 A1 | 4/2020 | Kostrzewski | |
| 2020/0237368 A1 | 7/2020 | Bruns et al. | |
| 2021/0077102 A1 | 3/2021 | Williams | |
| 2021/0307743 A1* | 10/2021 | Cappola | A61B 17/07207 |
| 2021/0346020 A1 | 11/2021 | Schings et al. | |
| 2024/0293119 A1* | 9/2024 | Laurent | A61B 17/105 |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0541950 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |

(56) References Cited

FOREIGN PATENT DOCUMENTS

| | | |
|---|---|---|
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| EP | 3138509 A1 | 3/2017 |
| EP | 3338660 A1 | 6/2018 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2013215572 A | 10/2013 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 2015191887 A1 | 12/2015 |
| WO | 2018161313 A1 | 9/2018 |
| WO | 2019186434 A1 | 10/2019 |

\* cited by examiner

SURGICAL STAPLING DEVICE WITH FIRING LOCKOUT

CROSS-REFERENCE TO RELATED APPLICATIONS

This application claims the benefit of and priority to U.S. Provisional Patent Application Ser. No. 63/278,586 filed Nov. 12, 2021, the entire disclosure of which is incorporated by reference herein.

FIELD

This disclosure relates to surgical stapling devices and, more particularly, to a surgical stapling device having a knife and a firing lockout mechanism.

BACKGROUND

Surgical stapling devices that eject staples to resect or transect tissue during surgical procedures are well known. These stapling devices are available in a variety of configurations including linear, curved, and circular, for performing open and endoscopic surgical procedures. Linear surgical stapling devices for performing open surgical procedures typically include an anvil section, a cartridge receiving section, a staple cartridge, and a firing assembly. The anvil section and the cartridge receiving section are coupled together and movable from an open position to a clamped position to clamp tissue between the staple cartridge and the anvil section. The staple cartridge is releasably secured within the cartridge receiving section, and the firing assembly is movable within the cartridge receiving section to eject the staples from the staple cartridge and to cut the tissue clamped between the staple cartridge and the anvil section.

These stapling devices often include a lockout assembly that prevents reclamping of the stapling device after the stapling device has been fired. In certain linear surgical stapling devices, the lockout assembly includes a knife guard that shields the knife and is movable after firing to a position to prevent reclamping of the stapling device. In such devices, the lockout may be susceptible to binding when staples come into contact the lockout assembly.

A continuing need exists in the art for a stapling device having a lockout assembly that is less susceptible to binding.

SUMMARY

This disclosure is directed to a surgical stapling device having an anvil section, a cartridge section, a staple cartridge, a clamping lever, and a firing assembly. The anvil section is coupled to the cartridge section and is movable in relation to the cartridge section between open and clamped positions in response to operation of the clamping lever. The staple cartridge is releasably supported on the cartridge section and includes a lockout assembly and a knife assembly. The knife assembly includes a knife bar having a cutting blade for cutting tissue clamped between the anvil and cartridge sections. The lockout assembly includes a lockout member that movable from an unlocked position to a locked position and is positioned to shield the cutting blade in both positions. The lockout member is configured to prevent binding of the lockout member after the stapling device is fired to ensure movement of the lockout member from the unlocked position to the locked position. In the locked position, the lockout member prevents movement of the anvil section in relation to the cartridge section to the clamped position.

Aspects of the disclosure are directed to a stapling device stapling device including an anvil section, a cartridge section, a firing assembly, a clamp member, and a staple cartridge. The anvil section has a proximal portion, a distal portion, and spaced beams. The proximal portion of the anvil section includes a hand grip, and the distal portion of the anvil section includes an anvil plate that is supported on the spaced beams. The cartridge section includes a channel member that defines a channel having a proximal portion and a distal portion. The channel member is adapted to be coupled to the anvil section to facilitate movement of the anvil section in relation to the cartridge section between open and clamped positions. The firing assembly is supported within the proximal portion of the channel and includes a drive beam and a trigger. The clamp member is supported on the cartridge section and is movable from an unclamped position to a clamped position to move the anvil section in relation to the cartridge section from the open position to the clamped position. The staple cartridge is releasably supported within the distal portion of the channel of the channel member of the cartridge section and includes a cartridge body, staples, pushers, an actuation sled, a knife assembly, and a lockout assembly. The cartridge body has a proximal portion and a distal portion and defines a central knife slot and staple receiving pockets positioned on opposite sides of the central knife slot. Each of the staple receiving pockets receives one of the staples and one of the pushers. The actuation sled is positioned within the proximal portion of the cartridge body and is movable through the cartridge body into engagement with the pushers to eject the staples from the staple receiving pockets. The knife assembly includes a knife bar having a cutting member that includes a member body having a distal edge and a cutting blade formed on the distal edge of the member body. The cutting blade is positioned within the knife slot and has an exposed portion that extends above the cartridge body. The lockout assembly includes a lockout member that is pivotably coupled to the proximal portion of the cartridge body and is movable from an unlocked position to a locked position. The lockout member has a base portion that defines a knife slot and includes a blade guard positioned on each side of the knife slot of the base portion. The knife slot of the base portion of the lockout member receives the drive beam of the firing assembly. The blade guards are positioned and configured to shield the exposed portion of the cutting blade when the lockout member is in the unlocked position while leaving the member body of the cutting member exposed. In the locked position, the lockout member obstructs movement of the anvil section in relation to the cartridge section from the open position to the clamped position.

Other aspects of the disclosure are directed to a staple cartridge including a cartridge body, staples, pushers, an actuation sled, a knife assembly, and a lockout assembly. The cartridge body has a proximal portion and a distal portion and defines a central knife slot and staple receiving pockets positioned on opposite sides of the central knife slot. Each of the staples is received one of the staple receiving pockets of the cartridge body. Each of the pushers is received within one of the staple receiving pockets of the cartridge body and supports one of the staples. The actuation sled is positioned within the proximal portion of the cartridge body and is movable through the cartridge body into engagement with the pushers to eject the staples from the staple receiving pockets. The knife assembly includes a knife bar that has a cutting member that includes a member body having a distal edge and a cutting blade formed on the distal edge of the member body. The cutting blade is positioned within the knife slot and has an exposed portion extending above the cartridge body. The lockout assembly includes a lockout member that is pivotably coupled to the proximal portion of the cartridge body and is movable from an unlocked position to a locked position. The lockout member has a base portion that defines a knife slot and includes a blade guard positioned on each side of the knife slot. The blade guards are positioned and configured to shield the exposed portion of the cutting blade when the lockout member is in the unlocked position while leaving the member body of the cutting member exposed.

In aspects of the disclosure, the staple cartridge includes a biasing member that is positioned to urge the lockout member towards the locked position.

In some aspects of the disclosure, the lockout member includes a blocking portion having a support block formed on each side of the knife slot of the base portion, and each of the support blocks has an engagement surface that is positioned to engage one of the spaced beams of the anvil section when the lockout member is in the locked position to prevent movement of the anvil section in relation to the cartridge section from the open position to the clamped position.

In certain aspects of the disclosure, the blocking portion has a distal portion positioned over but spaced from the knife bar when the lockout member is in the unlocked position and positioned distally of the knife bar when the lockout member is in the locked position.

In aspects of the disclosure, the distal portion of the blocking portion of the lockout member has an arcuate inner surface that faces the knife bar and a linear outer surface.

In some aspects of the disclosure, the base portion of the lockout member includes pivot members that are coupled to the cartridge body to pivotably couple the lockout member to the cartridge body.

In certain aspects of the disclosure, the biasing member includes a torsion spring that is positioned about one of the pivot members.

In aspects of the disclosure, the knife assembly includes a support member that supports the knife bar.

In some aspects of the disclosure, the support member is positioned within the cartridge body proximally of the actuation sled and is movable into engagement with the actuation sled to advance the actuation sled through the cartridge body.

In certain aspects of the disclosure, the knife bar includes a hook member that is configured to be coupled to the drive beam of the firing assembly when the staple cartridge is positioned within the channel of the channel member.

In aspects of the disclosure, the knife bar includes a retainer that engages the lockout member when the lockout member is in the unlocked position to retain the lockout member in the unlocked position.

Other aspects, features, and advantages will be apparent from the description, the drawings, and the claims that follow.

BRIEF DESCRIPTION OF THE DRAWINGS

Various aspects of the disclosure are described herein below with reference to the drawings, wherein.

DETAILED DESCRIPTION

Figure 1:
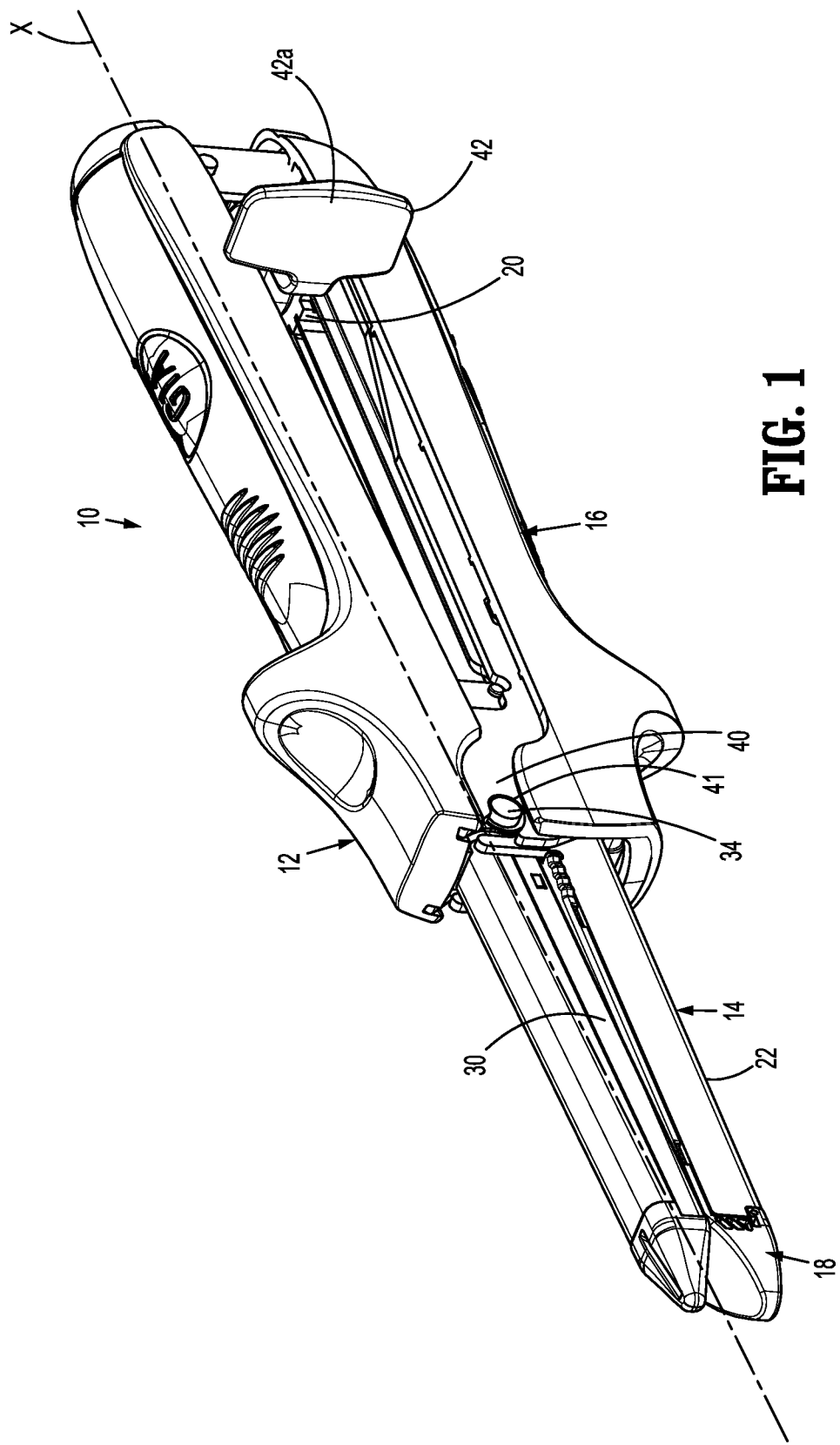
FIG. 1 is a side perspective view of a surgical stapling device according to aspects of the disclosure in a clamped pre-fired position.

The disclosed surgical device will now be described in detail with reference to the drawings in which like reference numerals designate identical or corresponding elements in each of the several views. However, it is to be understood that aspects of the disclosure are merely exemplary of the disclosure and may be embodied in various forms, Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel. Further, directional terms such as "front", "rear", "upper", "lower", "top", "bottom", and similar terms are used to assist in understanding the description and are not intended to limit the disclosure.

This disclosure is directed to a surgical stapling device that includes an anvil section, a cartridge section, a staple cartridge, a clamping lever, and a firing assembly. The staple cartridge is releasably supported on the cartridge section and includes a lockout assembly and a knife assembly. The anvil and cartridge sections are coupled together and movable from an open position to a clamped position in response to movement of the clamping lever from an unclamped position to a clamped position. The firing assembly is coupled to the knife assembly when the staple cartridge is received within the cartridge section and is movable between a retracted position and an advanced position to eject staples from the staple cartridge and to cut tissue clamped between the staple cartridge and the anvil section. The lockout assembly is supported on the staple cartridge and is movable from an unlocked position to a locked position to prevent reclamping of the anvil and cartridge sections after the stapling device has been fired. The lockout assembly includes a lockout member that is configured to prevent binding of the lockout member to ensure movement of the lockout member from the unlocked position to the locked position after the stapling device is fired and the anvil and cartridge sections are moved to the unclamped position.

Figure 2:
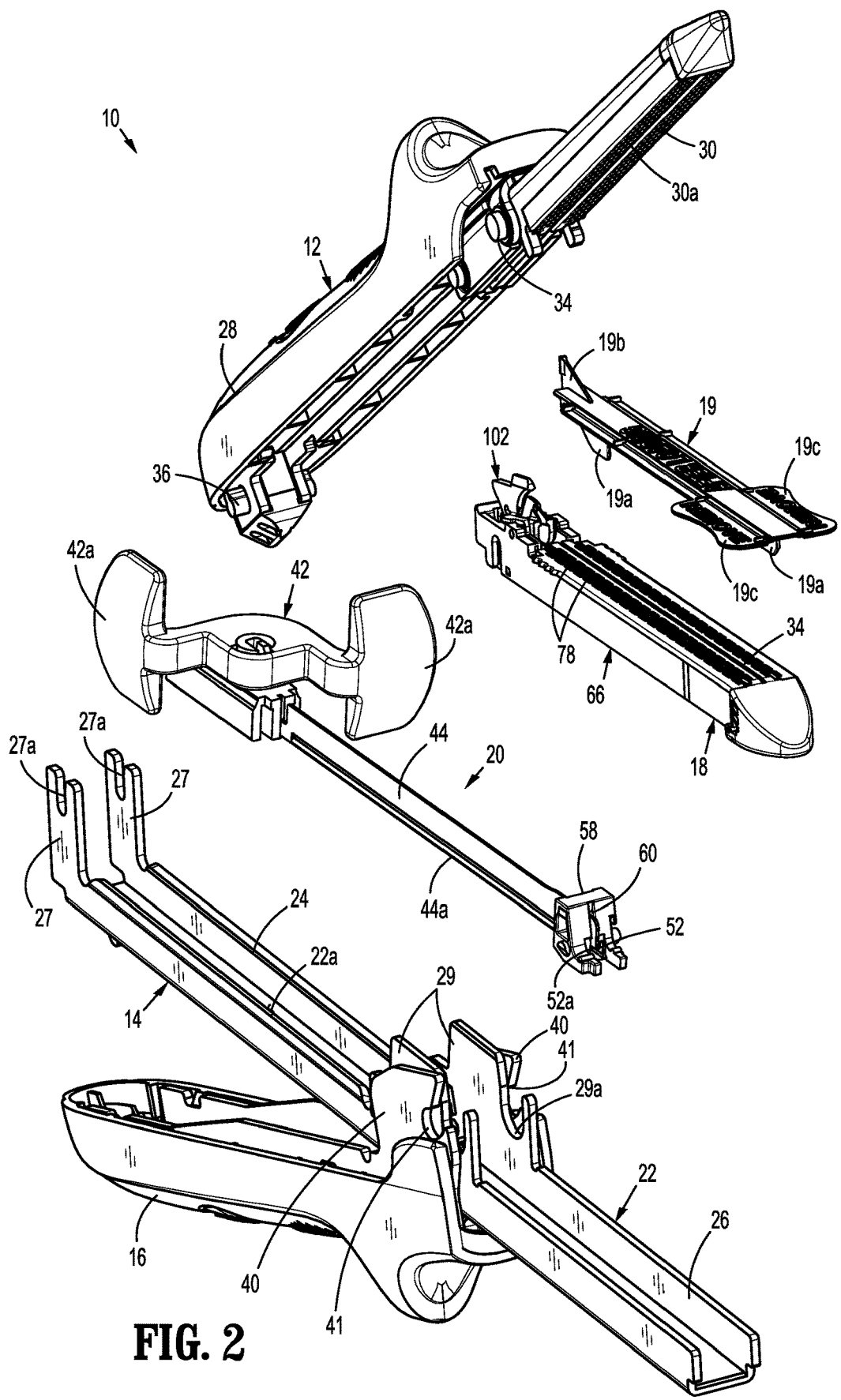
FIG. 2 is a perspective exploded view of the surgical stapling device shown in FIG. 1.

FIGS. 1 and 2 illustrate a surgical stapling device shown generally as stapling device 10. The stapling device 10 defines a longitudinal axis "X" (FIG. 1) and includes an anvil section 12, a cartridge section 14, a clamping lever 16, a staple cartridge 18, a shipping wedge 19 (FIG. 2), and a firing assembly 20, The cartridge section 14 includes a channel member 22 that has a proximal portion 24 and a distal portion 26 and defines a channel 22a that extends through the proximal and distal portions 24 and 26. The proximal portion 24 of the channel member 22 receives the firing assembly 20, and the distal portion 26 of the channel 22a receives the staple cartridge 18 in a manner to facilitate replacement of the staple cartridge 18 and reuse of the stapling device 10, The proximal portion 24 of the channel member 22 includes arms 27 that extend upwardly towards the anvil section 12 and define open ended recesses 27a. A central portion of the channel member 22 includes upwardly extending flanges 29 that define circular cavities 29a.

The anvil section 12 includes spaced beams 12a and 12b (FIG. 18), an anvil hand grip 28 supported on a proximal portion of the beams 12a and 12b, and an anvil plate 30 supported on a distal portion of the beams 12a and 12b. The anvil plate 30 defines a knife slot 30a and faces the cartridge section 14 when the anvil section 12 and the cartridge section 14 are coupled together. The anvil section 12 also includes protrusions 34 that are centrally located on the anvil section 12 and pivot members 36 that are located on a proximal portion of the anvil section 12. The pivot members 36 are received within the recesses 27a of the arms 27 of the channel member 22 to pivotally support the proximal portion of the anvil section 12 on the proximal portion of the cartridge section 14 and facilitate movement of the anvil section 12 in relation to the cartridge section between open and clamped positions. The protrusions 34 are received within the circular cavities 29a of the flanges 29 of the channel member 22 when the anvil section 12 is coupled to the cartridge section 14. In aspects of the disclosure, the pivot members 36 have a tear-shaped configuration although other configurations are envisioned. In the clamped position of the anvil and cartridge sections 12 and 14, the anvil plate 30 is in juxtaposed relation to the staple cartridge 18.

The clamping lever 16 is pivotally supported on a proximal portion of the cartridge body 14 and is movable between an unclamped position and a clamped position. The clamping lever 16 includes centrally located flanges 40 that are spaced from each other and positioned on opposite sides of the cartridge section 14. Each of the spaced flanges 40 defines a recess 41 that receives one of the protrusions 34 of the anvil section 12 when the clamp lever 16 is pivoted from an unclamped position to a clamped position to move the protrusions 34 of the anvil section 12 further into the cavities 29a of the flanges 29 of the channel member 22 to move the anvil section 12 into juxtaposed alignment with the cartridge section 14 and to clamp tissue between the anvil plate 30 and the staple cartridge 18.

FIG. 2 illustrates the firing assembly 20 which includes a trigger 42 and a longitudinally extending drive beam 44. The trigger 42 is rotatably supported on a proximal portion of the drive beam 44 and includes a thumb engagement member 42a positioned on each side of the stapling device 10. The thumb engagement member 42a is rotatable between two positions to facilitate actuation of the stapling device 10 from both sides of the stapling device 10. The pivotable trigger 42 is coupled to a proximal portion of the drive beam 44 and is movable longitudinally within the proximal portion 24 of the channel 22a of the channel member 22 of the cartridge section 14 to advance the drive beam 44 from a retracted position to an advanced position. The drive beam 44 includes a distal portion that is adapted to engage a knife assembly 50 (FIG. 4) of the staple cartridge 18 when the staple cartridge 18 is received within the distal portion 26 of the channel member 22. In aspects of the disclosure, the distal portion of the drive beam 44 includes a hook-shaped portion 52 that extends upwardly towards the anvil section 12 and defines a slot 52a having an open upper end as viewed in FIG. 2. In aspects of the disclosure, the drive beam 44 includes a longitudinally extending rib 44a formed along a lower end of the drive beam 44. The rib 44b adds rigidity to the drive beam 44 to prevent buckling of the drive beam 44 during firing of the stapling device 10. In certain aspects of the disclosure, the rib 44a can be formed by rolling the lower end of the drive beam 44 upwardly. Alternately, the rib 44a can be formed on or applied to drive beam 44 using a variety of different techniques.

A lock member 58 (FIG. 2) is supported within a central portion of the channel 22a of the channel member 22 of the cartridge section 14. The lock member 58 defines a slot 60 (FIG. 2) that receives the drive beam 44 to facilitate movement of the drive beam 44 between the retracted and advanced positions. The lock member 58 is pivotable between a locked position in which the lock member 58 is engaged with the drive beam 44 and an unlocked position in which the lock member 58 is positioned to allow the drive beam 44 to move through the slot 60. In aspects of the disclosure, the lock member 58 is pivotable from the locked position to the unlocked position in response to placement of a staple cartridge 18 within the channel 22a in the distal portion 26 of the channel member 22 of the cartridge section. In some aspects of the disclosure, a biasing member (not shown) is engaged with the lock member 58 to urge the lock member 58 towards the locked position.

Figure 3:
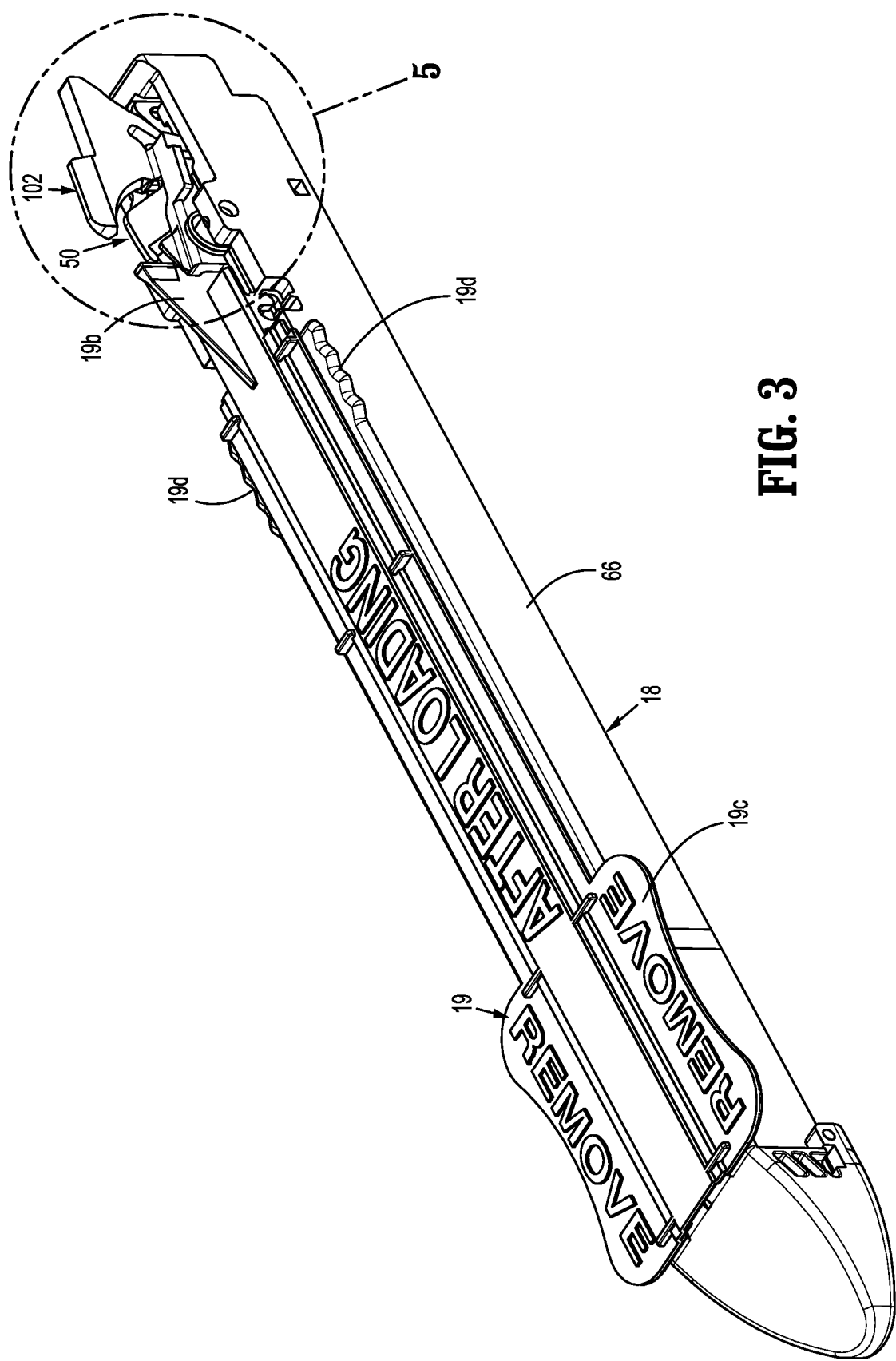
FIG. 3 is a side perspective view of a staple cartridge and shipping wedge of the surgical stapling device shown in FIG. 2.
Figure 4:
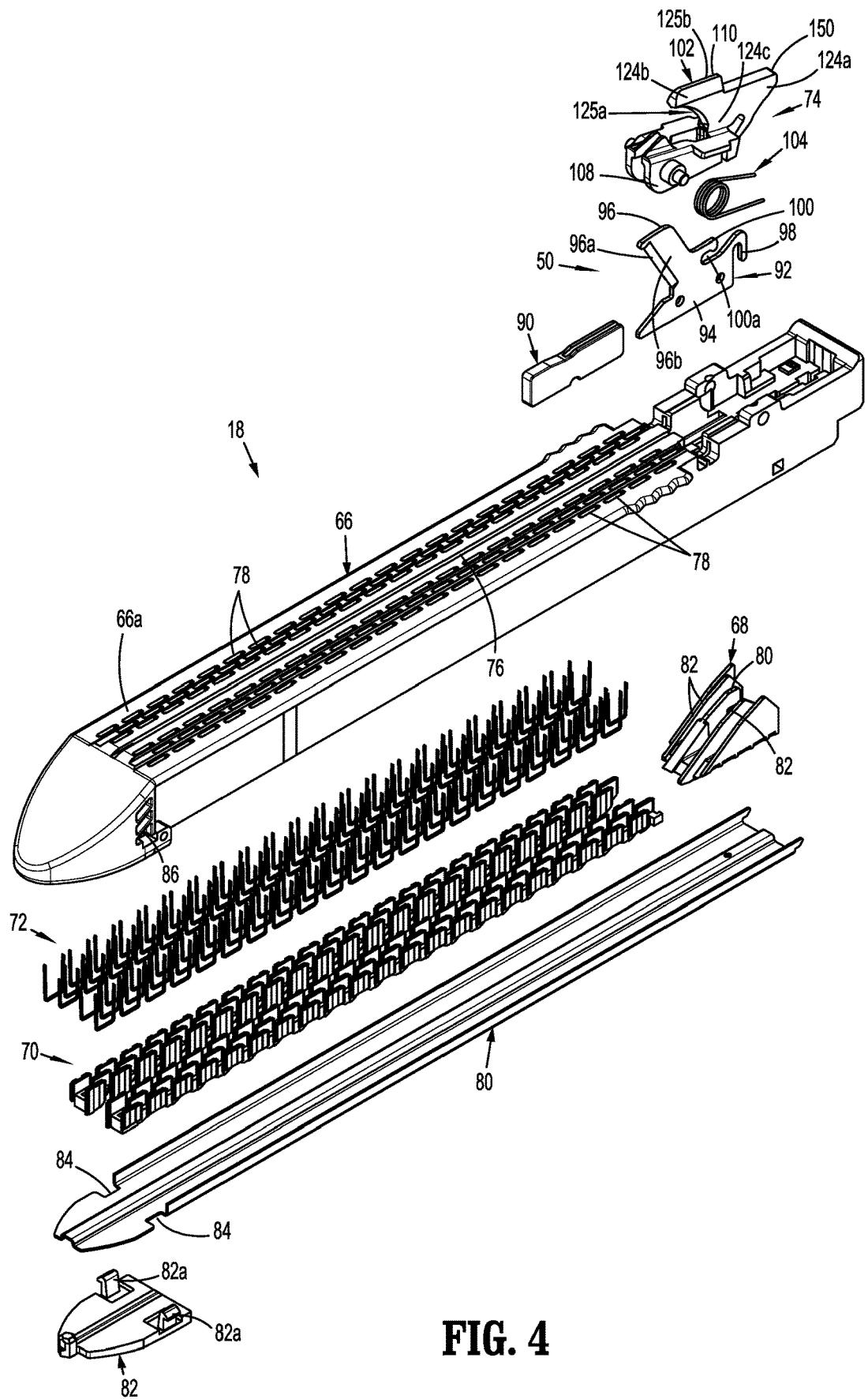
FIG. 4 is an enlarged view of the indicated area of detail shown in FIG. 5.
Figure 5:
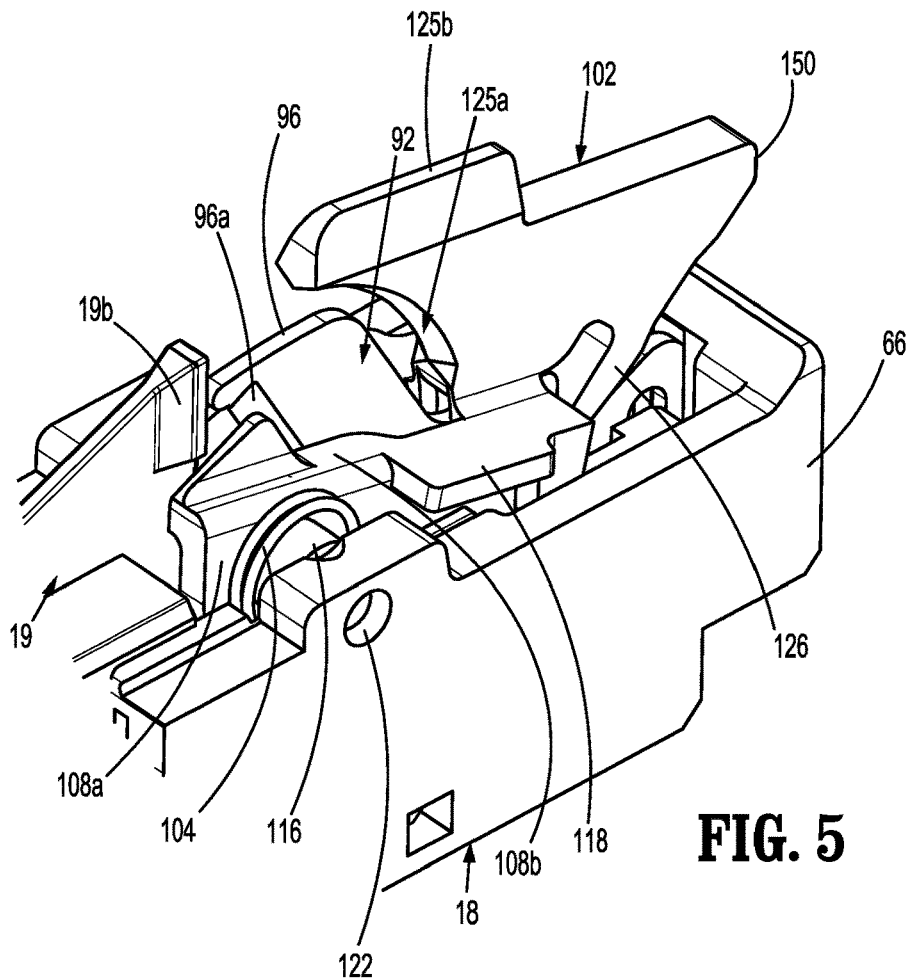
FIG. 5 is a side perspective view of a proximal portion of the staple cartridge shown in FIG. 3.
Figure 6:
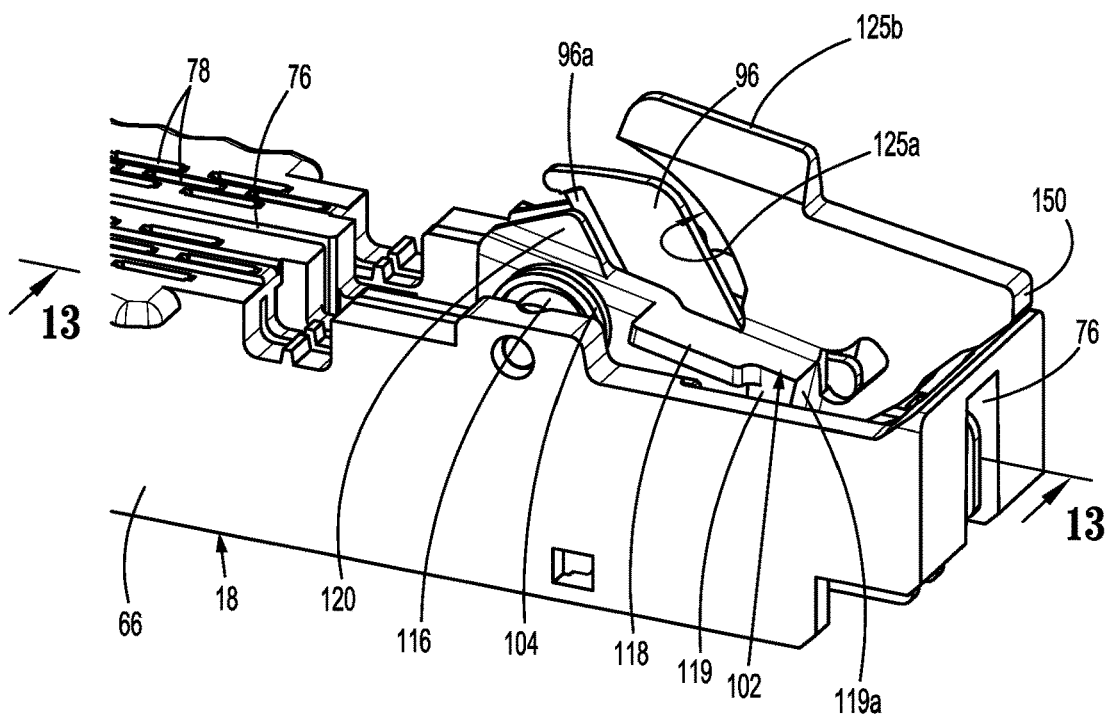
FIG. 6 is a side perspective exploded view of the staple cartridge shown in FIG. 2.

FIGS. 2-4 illustrate the staple cartridge 18 which includes a cartridge body 66, the knife assembly 50, an actuation sled 68, pushers 70, staples 72, and a lockout assembly 74, The cartridge body 66 includes a tissue contact surface 66a that defines a centrally located knife slot 76 and staple receiving pockets 78 that are positioned on opposite sides of the knife slot 76. The knife slot 76 extends through the staple cartridge 18 from a proximal end of the staple cartridge 18 to a position adjacent a distal end of the staple cartridge 18. The knife assembly 50 is movable through the knife slot 76 from a retracted position to an advanced position when the drive bar 44 (FIG. 2) of the firing assembly 20 is advanced from a retracted position to an advanced position to cut tissue clamped between the anvil plate 30 and the staple cartridge 18.

Each of the staple receiving pockets 78 receive one of the staples 72 and one of the pushers 70. In aspects of the disclosure, the staple receiving pockets 78 are aligned in two or more rows on the opposite sides of the knife slot 76, e.g., three. The actuation sled 68 is supported within the cartridge body 66 and includes a central rib 80 (FIG. 4) and cam surfaces 82 positioned on opposite sides of the central rib 80. The central rib 80 is received in the knife slot 76 of the cartridge body 66 and the cam surfaces 82 are aligned with the pushers 70. The actuation sled 68 is movable from a retracted position to an advanced position within the cartridge body 66 in response to movement drive beam from its retracted position to its distal position into engagement with the pushers 70 to eject the staples 72 from the staple receiving slots 78 of the cartridge body.

The staple cartridge 18 also includes a staple guard 80 that is secured to a lower portion of the cartridge body 66 to retain the staples 72 and the pushers 70 within the staple receiving pockets 78 of the cartridge body 66. In aspects of the disclosure, the staple guard 80 is secured to the cartridge body 66 with a connector 82 that includes spaced flexible detents 82a. the detents 82a extend through cutouts 84 defined in the staple guard 80 and slots 86 formed in a distal portion of the cartridge body 66 to secure the staple guard 80 to the cartridge body 66 in snap-fit fashion.

The shipping wedge 19 (FIG. 3) is secured to the tissue contact surface 66a (FIG. 4) of the cartridge body 66 and is provided to retain the knife assembly 50 in a retracted position and retain the staples 72 within the cartridge body 66. In aspects of the disclosure, the shipping wedge 19 includes fins 19a (FIG. 2) that are received in the knife slot 76 of the cartridge body 66 to secure the shipping wedge 19 to the cartridge body 66. When the shipping wedge 19 is secured to the cartridge body 66, the shipping wedge 19 covers the staple receiving slots 78. The shipping wedge 19 includes a stop member 19b (FIG. 2) that is positioned to prevent advancement of the knife assembly 74 until the shipping wedge 19 is removed from the cartridge body 66. The shipping wedge 19 includes lateral extensions 19c positioned on a distal portion of the shipping wedge 19 and serrations 19d positioned on a proximal portion of the shipping wedge 19 that can be grasped by a clinician to remove the shipping wedge 19 from the staple cartridge 18.

The knife assembly 50 includes a support member 90 and a knife bar 92. The knife bar 92 includes base 94, a cutting member 96 that extends upwardly from the base 94, a hook member 98, and a retainer 100. The knife bar 92 is secured to the support member 90 such that the knife assembly 50 is movable as a single construct through the cartridge body 66. The cutting member 96 includes a member body 96b that extends upwardly from the base 94 and has a cutting blade 96a that is formed on a distal edge of the member body 96. In aspects of the disclosure, the cutting member 96 extends from the base at an angle such that the uppermost end of the cutting blade 96a is position distally of the lowermost end of the cutting blade 96a. The hook member 98 of the knife bar 92 is formed on a proximal portion of the knife bar 92 and extends downwardly. The hook member 98 is received within the slot 52a (FIG. 2) defined by the hook-shaped portion 52 of the drive beam 44 when the staple cartridge 18 is received in the distal portion 26 of the cartridge section 14. The retainer 100 of the knife bar 92 is positioned on a central portion of the knife bar 92 and extends proximally to define a retaining slot 100a that receives a portion of the lockout assembly 74 to retain the lockout assembly 74 in a locked position as described in further detail below. For a more detailed description of the components of the stapling device described above, see, e.g., U.S. Pat. No. 8,505,801 to Ehrenfels et al.

FIGS. 4-12 illustrate the lockout assembly 74 which includes a lockout member 102 and a biasing member 104, The lockout member 102 has a base 108 and a blocking portion 110 that is secured to a central portion of the base 108. The base 108 defines a longitudinal slot 114 (FIG. 9) and includes side walls 108a, an upper surface 108b, pivot members 116, laterally extending wings 118, and cutting blade guards 120. The pivot members 116 are formed on a distal portion of the base 108 and extend outwardly from the side walls 108a. The pivot members 116 are received in openings 122 defined in the proximal portion of the cartridge body 66 of the staple cartridge 18 to pivotally couple the lockout member 102 to the cartridge body 66 such that the lockout member 102 is movable from an unlocked position to a locked position.

The laterally extending wings 118 are formed on a proximal portion of the base 108 of the lockout member 102 and extend outwardly of the side walls 108a of the base 108 of the lockout member 102. When the lockout member 102 is in the unlocked position, the wings 118 rest on the beams 12a and 12b of the anvil section 12 to minimize deflection of the lockout member 102.

Figure 18:
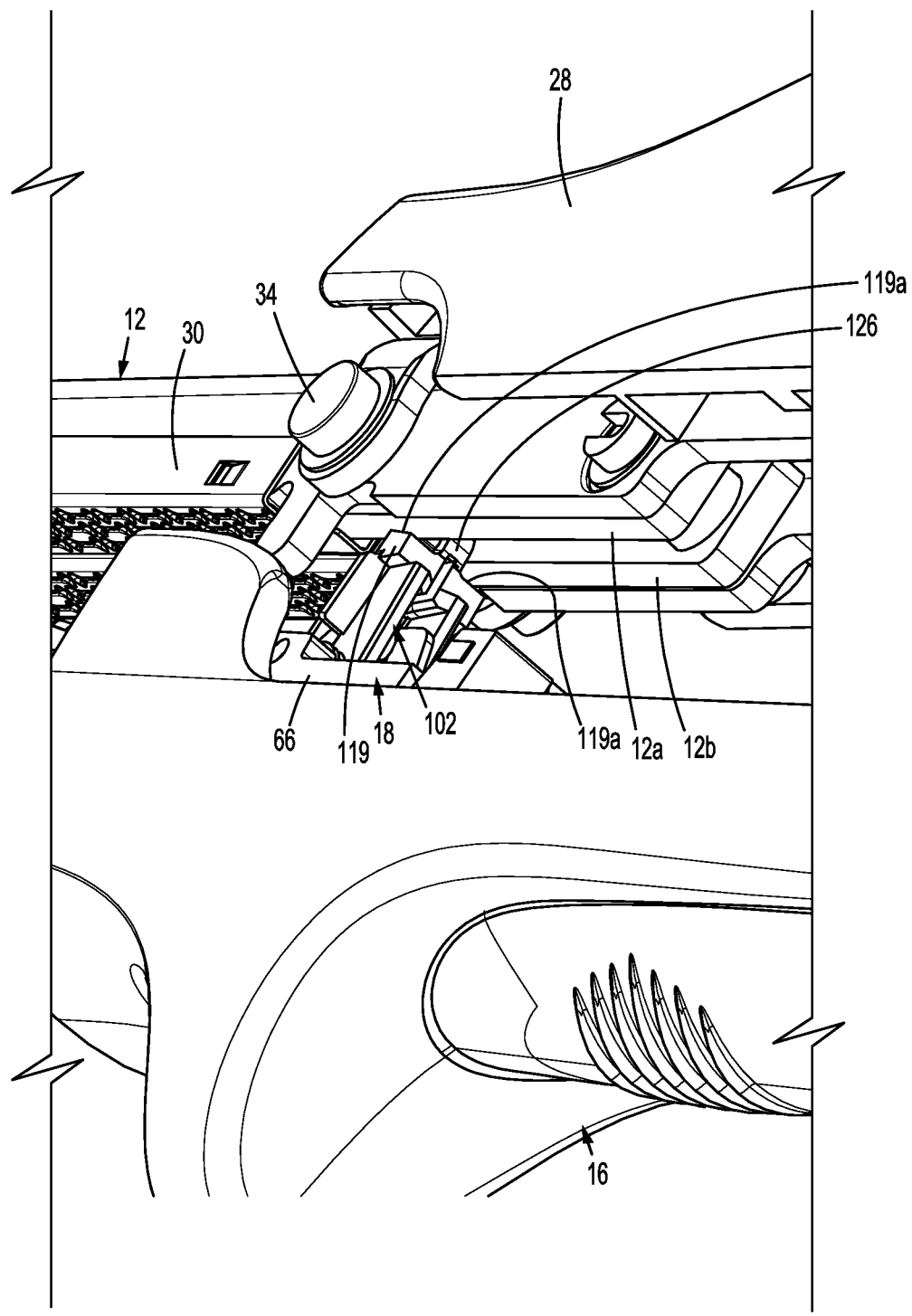
FIG. 18 is a side perspective, cutaway view of the central portion of the stapling device shown in FIG. 16.

In aspects of the disclosure, the proximal portion of the base 108 of the lockout member 102 includes support blocks 119 that are symmetrically positioned on opposite sides of the longitudinal slot 114 on the proximal end of the base 108 of the lockout member 102. The support blocks 119 include engagement surfaces 119a that are substantially vertically oriented and face proximally when the lockout member 102 is in the unlocked position and are substantially horizontally oriented and face the anvil section 12 when the lockout member 102 is in the locked position (FIG. 18). The support blocks 119 include engagement surfaces 119a that engage the beams 12a and 12b of the anvil section when the lockout member 102 is in the locked position and the anvil section 12 is coupled to a cartridge section 14 having a spent or fired staple cartridge 18 to prevent reclamping of the stapling device 10. The increased surface area provided by the engagement surfaces 119a minimizes deflection of the lockout member 102 when the lockout member 102 is in the locked position and an attempt is made to attach an anvil section 12 to the cartridge section 14.

The cutting blade guards 120 are formed on opposite sides of the longitudinal slot 114 on the distal portion of the base 108 of the lockout member 102. In aspects of the disclosure, the cutting blade guards 120 are triangular and have proximal walls 120a that extend in the direction of the cutting blade 96a of the cutting member 96 of the knife bar 92. The cutting blade guards 120 are positioned on opposite sides of the cutting blade 96a to shield the cutting blade 96a. In aspects of the disclosure, the cutting blade guards 120 or positioned distally of the member body 96b of the cutting member 96 to minimize any likelihood of staples becoming wedged between the cutting blade guards 120 and the cutting member 96 of the knife bar 92.

Figure 7:
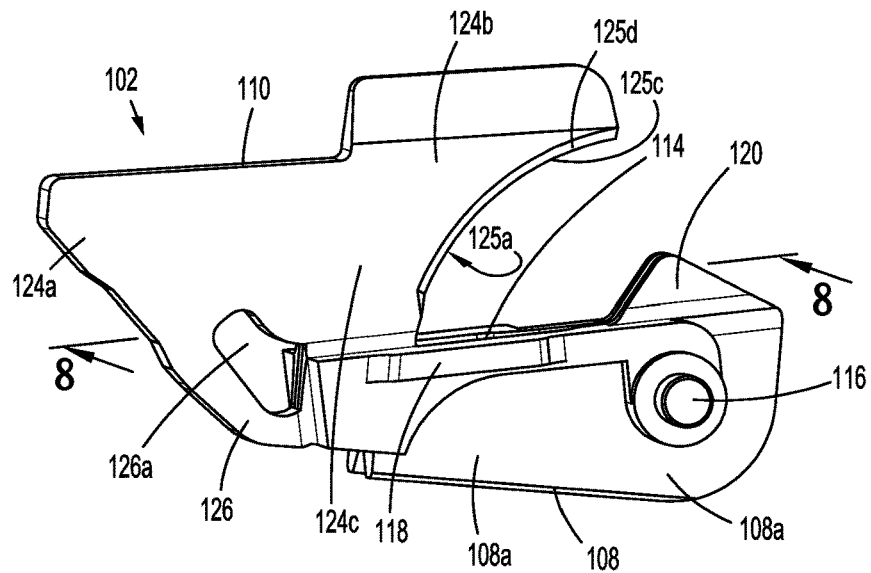
FIG. 7 is a side perspective view of a lockout member of the staple cartridge shown in FIG. 6.
Figure 8:
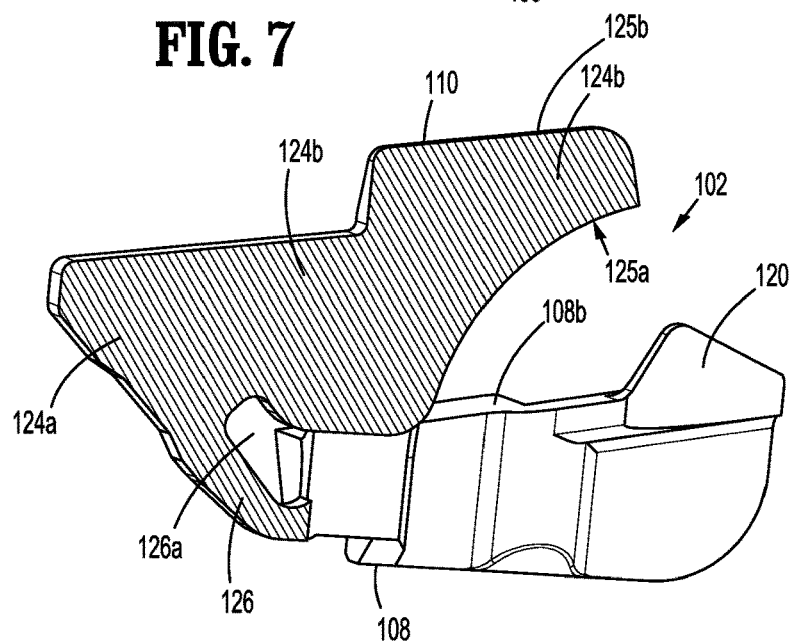
FIG. 8 is a cross-sectional view taken along section line 8-8 of FIG. 7.
Figure 9:
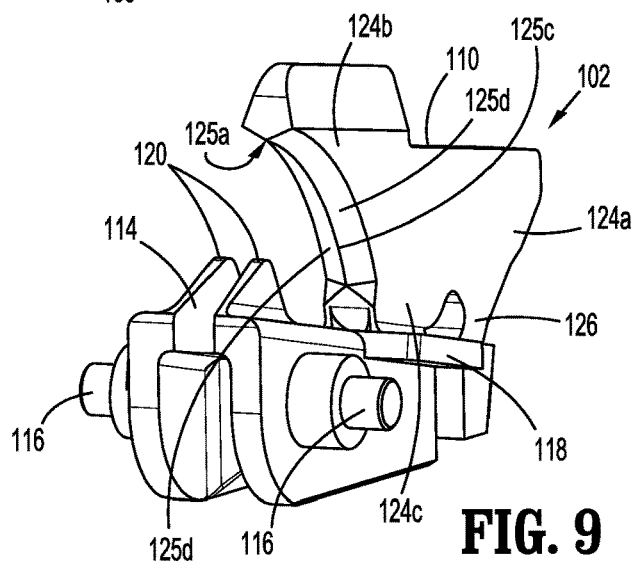
FIG. 9 is a perspective view from the proximal end of the lockout member shown in FIG. 7.
Figure 10:
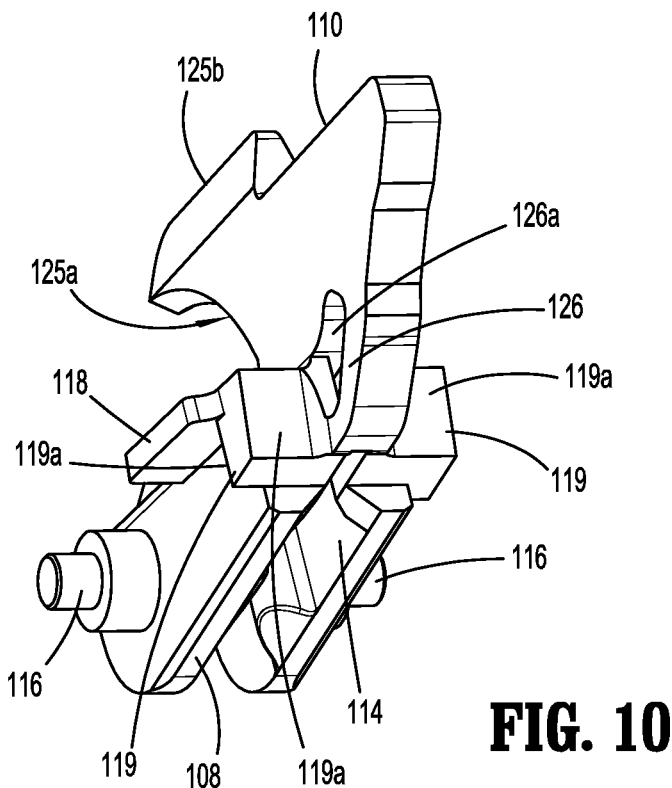
FIG. 10 is a bottom perspective view from the distal end of the lockout member shown in FIG. 7.
Figure 11:
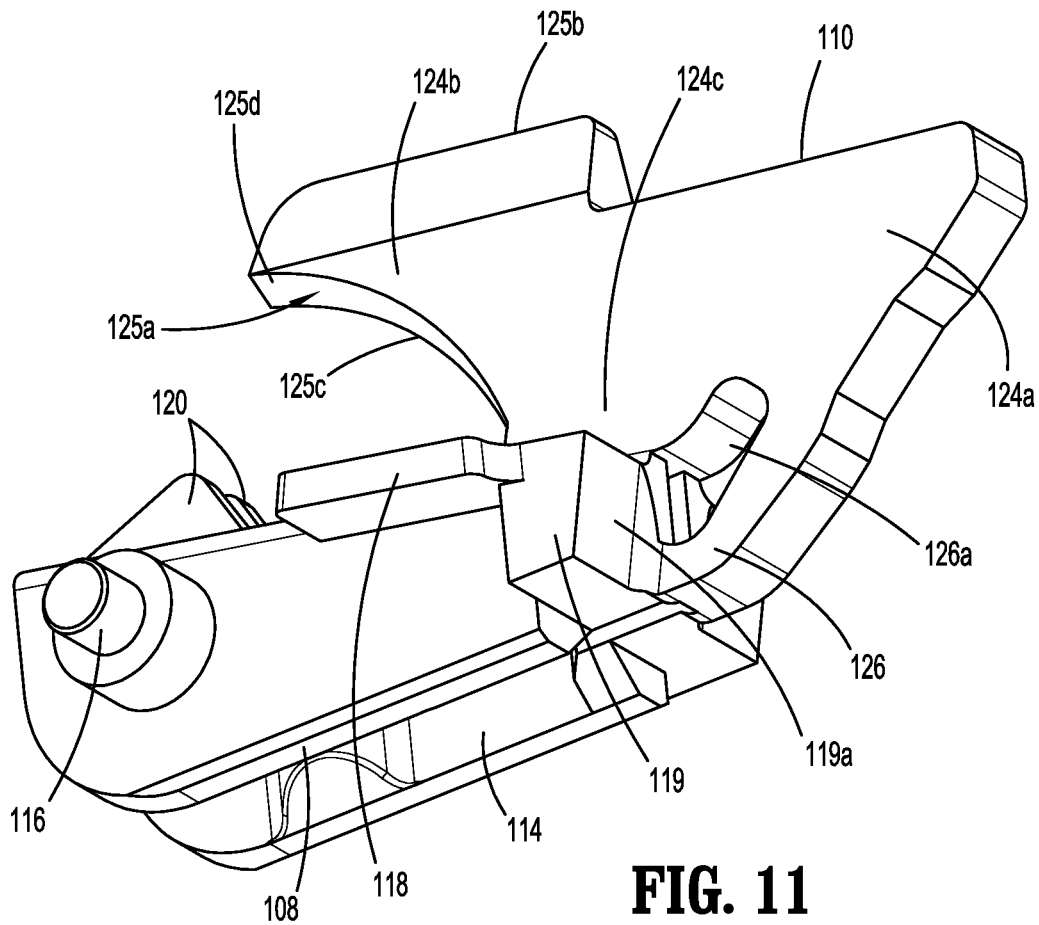
FIG. 11 is a side perspective view from below of the lockout member shown in FIG.
Figure 12:
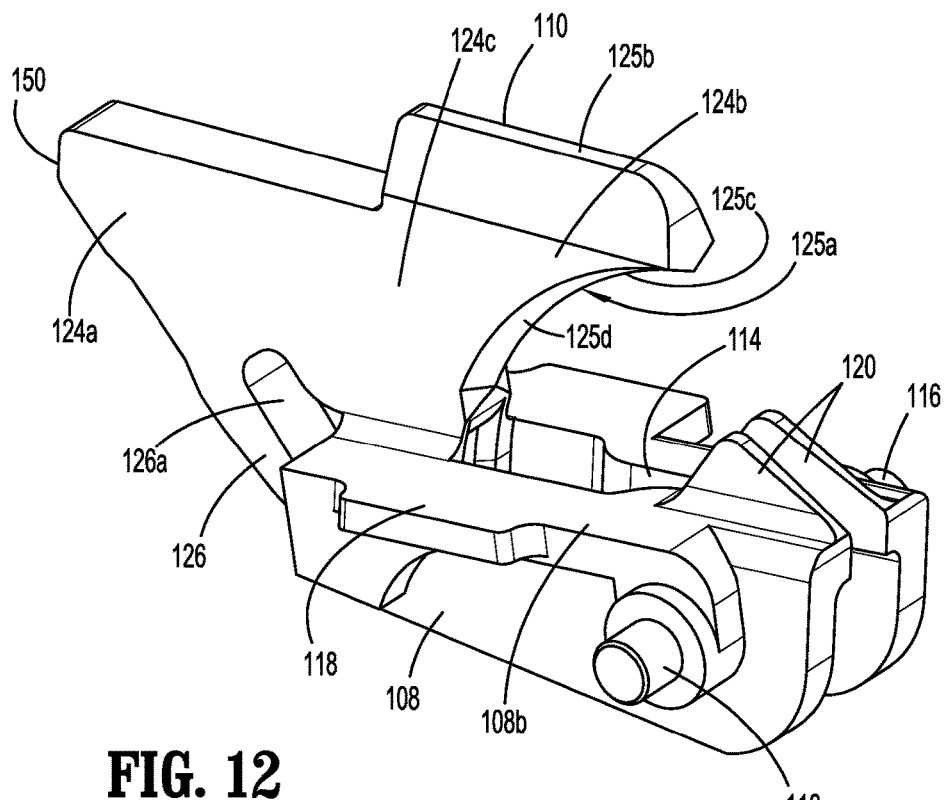
FIG. 12 is a side perspective view from above of the lockout member shown in FIG. 7.

The blocking portion 110 includes a body 124 having a proximal portion 124a, a distal portion 124b, and a central portion 124c (FIG. 7). The central portion 124c (FIG. 7) is coupled to or integrally formed with the base 108 of the lockout member 102. The distal portion 124b of the blocking portion 110 has an arcuate inner surface 125a and a linear outer surface 125b. The arcuate inner surface 125a has a triangular configuration and includes a central ridge 125c and angled walls 125d that extend outwardly from the central ridge 125c. The distal portion 124b of the blocking portion 110 and extends over but is spaced from the cutting member 96 of the (FIG. 6) when the knife bar 92 when the lockout member 102 is in the unlocked position. The proximal portion 124a of the blocking portion 110 of the lockout member 102 has a distal extension 126 that defines a cavity 126a that receives the retainer 100 of the knife bar 92 when the knife bar 92 is in its retracted position. Receipt of the retainer 100 within the cavity 126a of the lockout member 102 retains the lockout member 102 in the unlocked position.

The biasing member 104 of the lockout assembly 74 is positioned to urge the lockout member 102 towards the locked position. In aspects of the disclosure, the biasing member 104 includes a torsion spring that is positioned about one (or both) of the pivot members 116 of the lockout member 102 to urge the lockout member 102 towards the locked position. Alternately, it is envisioned that the biasing member 104 may have a variety of configurations.

Figure 13:
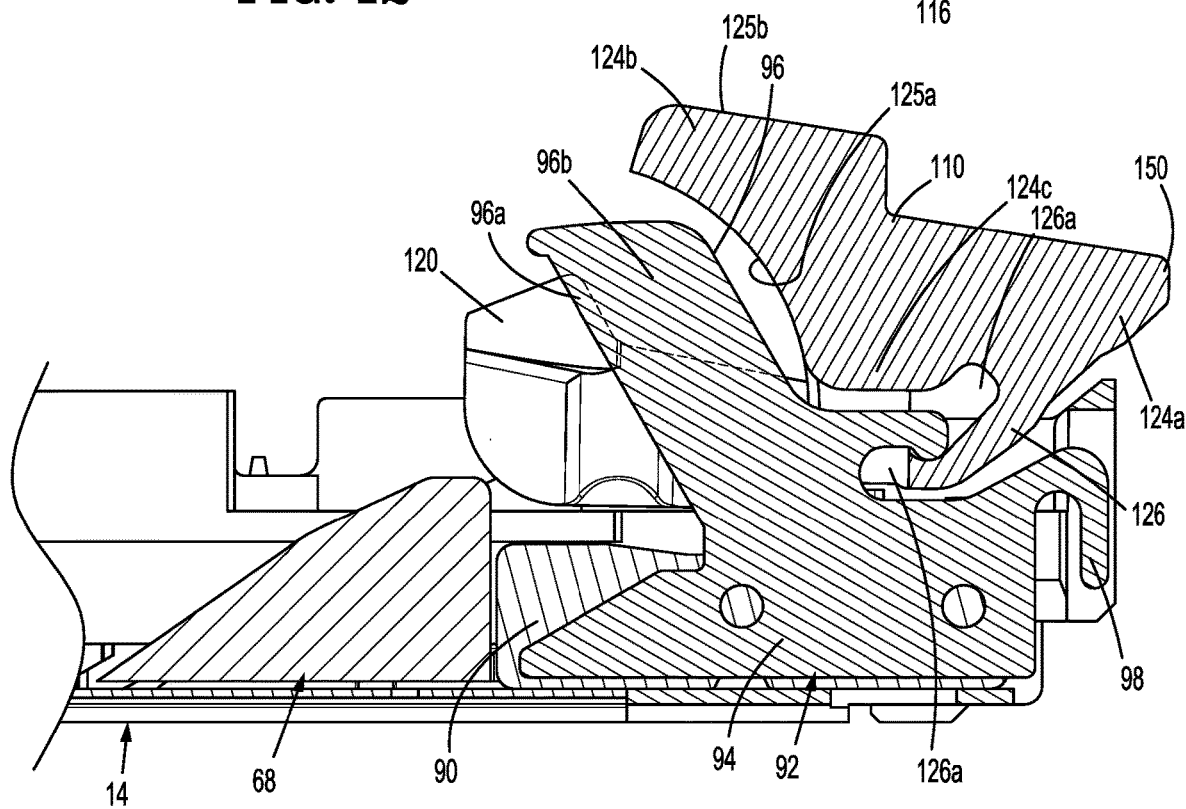
FIG. 13 is a cross-sectional view taken through the proximal portion of a channel member and staple cartridge of the surgical stapling device shown in FIG. 2 in a pre-fired position.

FIG. 13 illustrates the proximal portion of the cartridge assembly 14 in a pre-fired condition with the firing assembly 20 and the knife assembly 50 in retracted positions. In the pre-fired condition, the retainer 100 of the knife bar 92 is received within the cavity 126a of the blocking portion 110 of the lockout member 102 to retain the lockout member 102 in the unlocked position. In the unlocked position, the upper portion of the cutting blade 96a is shielded by the cutting blade guards 120 and the lower position of the cutting blade 96a is positioned within the longitudinal slot 114 of the lockout member 102. The distal portion 124b of the blocking portion 110 of the lockout member 102 is positioned over a portion of the member body 96b of the cutting member 96 when the lockout member 102 is in the unlocked position.

When the stapling device 10 (FIG. 1) is fired by pressing on one of the thumb engagement members 42a of the pivotable trigger 42 to move the firing assembly 20 and the knife assembly 50 to their advanced positions, the retainer 100 of the knife bar 92 is removed from the cavity 126 of the lockout member 102 to release the lockout member 102. When the lockout member 102 is released, the biasing member 104 of the lockout assembly 74 rotates the lockout member 102 in a counterclockwise direction as indicated by arrow "A" in FIG. 15 towards the locked position. In the locked position, the distal portion 124b of the blocking portion 110 of the lockout member 102 extends downwardly from above the knife assembly 50 to a position in front or distally of the cutting blade 96a of the knife bar 92 of the knife assembly 50 to shield the cutting blade 96a of the knife bar 92. It is noted that movement of the lockout member 102 from the unlocked position to the locked position is obstructed by the anvil section 12 when the stapling device 10 is in the clamped position. Thus, the lockout member 102 will not move to the locked position until the stapling device 10 is unclamped, i.e., the clamping lever 16 is moved to the unclamped position to space the anvil section 12 from the cartridge section 14.

When the stapling device 10 (FIG. 1) is fired and the knife bar 92 is moved to its advanced position, the actuation sled 68 (FIG. 13) is engaged by the support member 90 (FIG. 4) of the knife assembly 50 and advanced through the cartridge body 66 into engagement with the pushers 70 to eject the staples 72 (FIG. 4) from the cartridge body 66. As the knife bar 92 of the knife assembly 50 moves through the knife slot 76 of the cartridge body 66, the cutting blade 96a of the cutting member 96, which projects above the cartridge body 66, cuts tissue clamped between the anvil section 12 and the cartridge section 14.

After the knife assembly 50 reaches its advanced position, the firing assembly 20 is returned to its retracted position by pushing or pulling the pivotable trigger 42 in a proximal direction. It is noted that the actuation sled 68 is not coupled to the knife assembly 50 and as such will remain in the distal portion of the cartridge body 66 when the firing assembly 20 and knife assembly 50 are returned to their retracted positions. When the knife assembly 50 reaches its retracted position, the retainer 100 of the knife bar 92 is no longer aligned with the cavity 126 of the lockout member 102 which has pivoted towards the locked position. As such, the lockout member 102 can rotate to its locked position when the stapling device 10 is moved to the unclamped position. As illustrated in FIG. 13, the arcuate surface 125a of the blocking portion 110 of the lockout member 102 is spaced proximally of the cutting member 96 when the lockout member 102 is in its unlocked position. The lockout member 102 will not move to the locked position after the stapling device 10 is fired until the anvil section 12 is spaced from the cartridge section 14 a sufficient distance from the cartridge section 14 to allow the lockout member to pivot. It is noted that the shape of the arcuate surface 125a of the lockout member 102 including the angled walls 125d directs staples that may be positioned between the cutting member 96 and the arcuate surface 125a outwardly of the arcuate surface 125a to prevent the staples from becoming trapped between the lockout member 102 and the cutting member 96 which may obstruct movement of the lockout member 102 from the unlocked position to the locked position.

Figure 14:
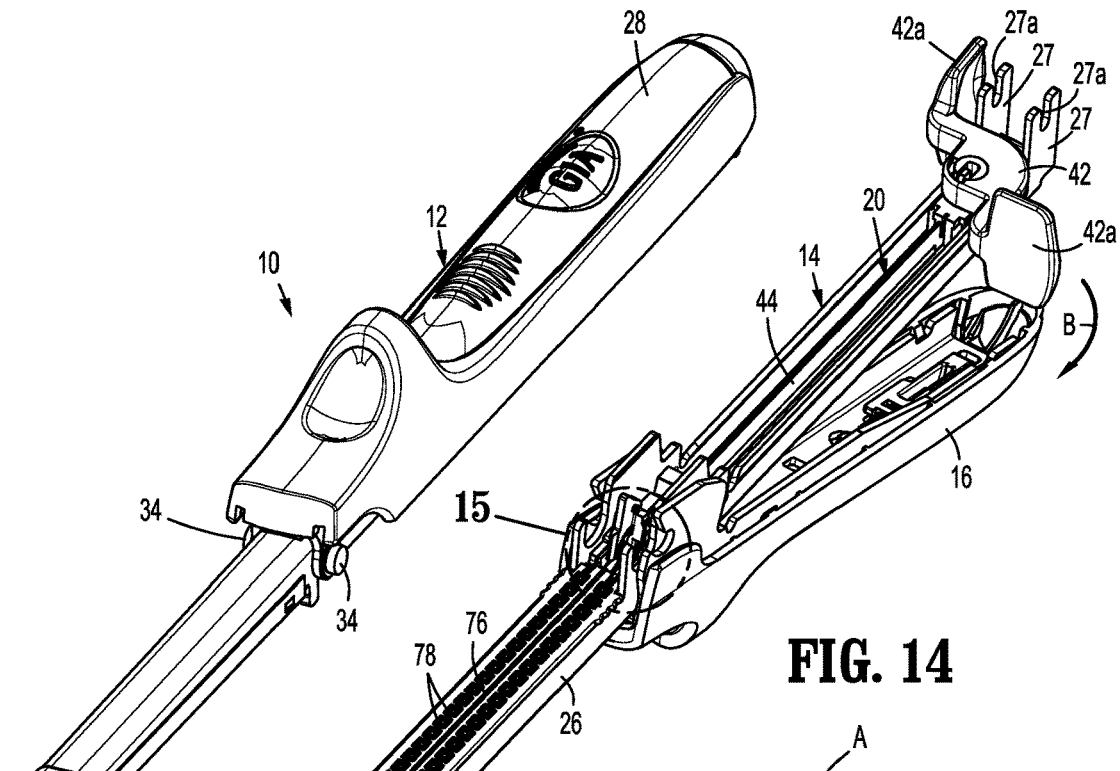
FIG. 14 is a side perspective view of the stapling device shown in FIG. 1 with the anvil section separated from the cartridge section after the stapling device has been fired.
Figure 15:
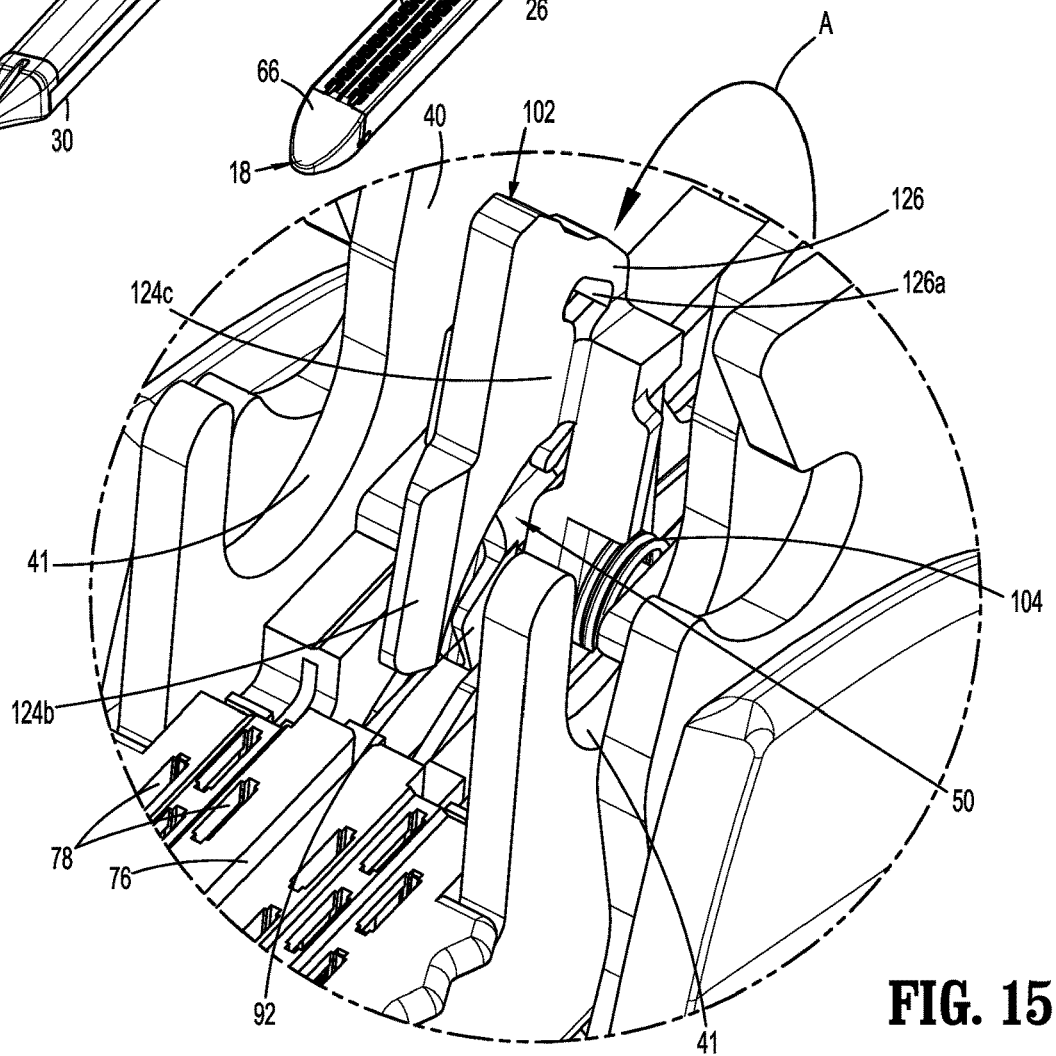
FIG. 15 is an enlarged view of the indicated area of detail shown in FIG. 14.

FIGS. 14 and 15 illustrate the stapling device 10 with the anvil section 12 separated from the cartridge section 14 after the stapling device 10 has been fired and the firing assembly 20 and the knife assembly 50 are returned to their retracted positions. Separation of the anvil section 12 from the cartridge section 14 allows the lockout member to rotate from the unlocked position towards the locked position and is accomplished by moving the clamping lever 16 in the direction indicated by arrow "B" in FIG. 14 to the unclamped position as is known in the art. When the lockout member 102 is in the locked position, the proximal portion 124a of the blocking portion 110 of the lockout member 102 extends upwardly from the proximal end of the staple cartridge 18 and the distal portion 124b of the blocking portion 110 of the lockout member 102 extends downwardly to a position in front of an exposed portion of the cutting blade 96a (FIG. 17).

Figure 16:
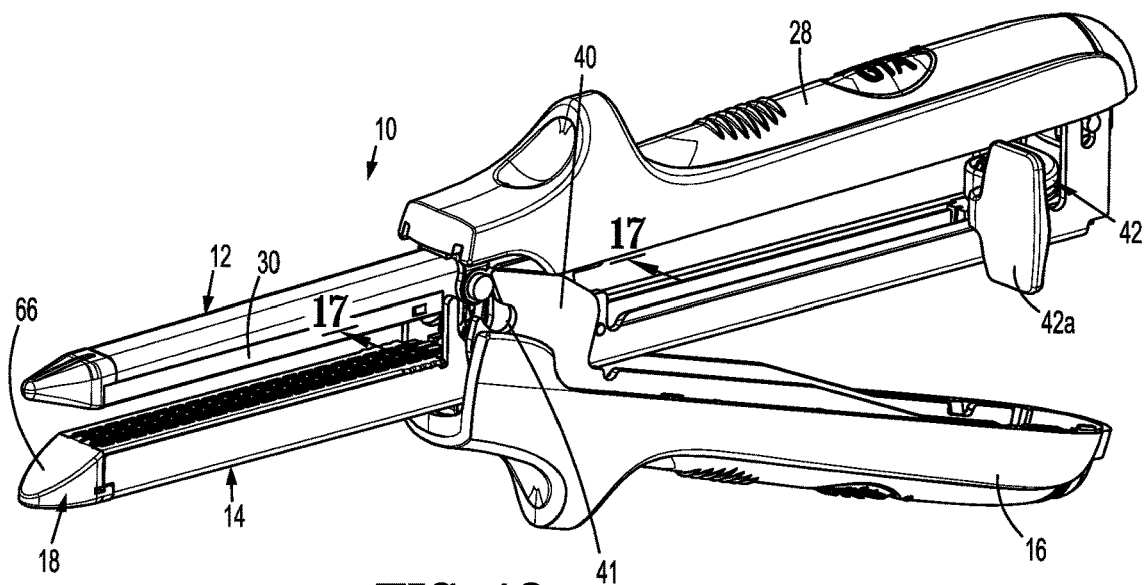
FIG. 16 is a side perspective view of the surgical stapling device shown in FIG. 1 with the cartridge section having a spent or fired staple cartridge as an anvil section is attempted to be coupled to the cartridge section.
Figure 17:
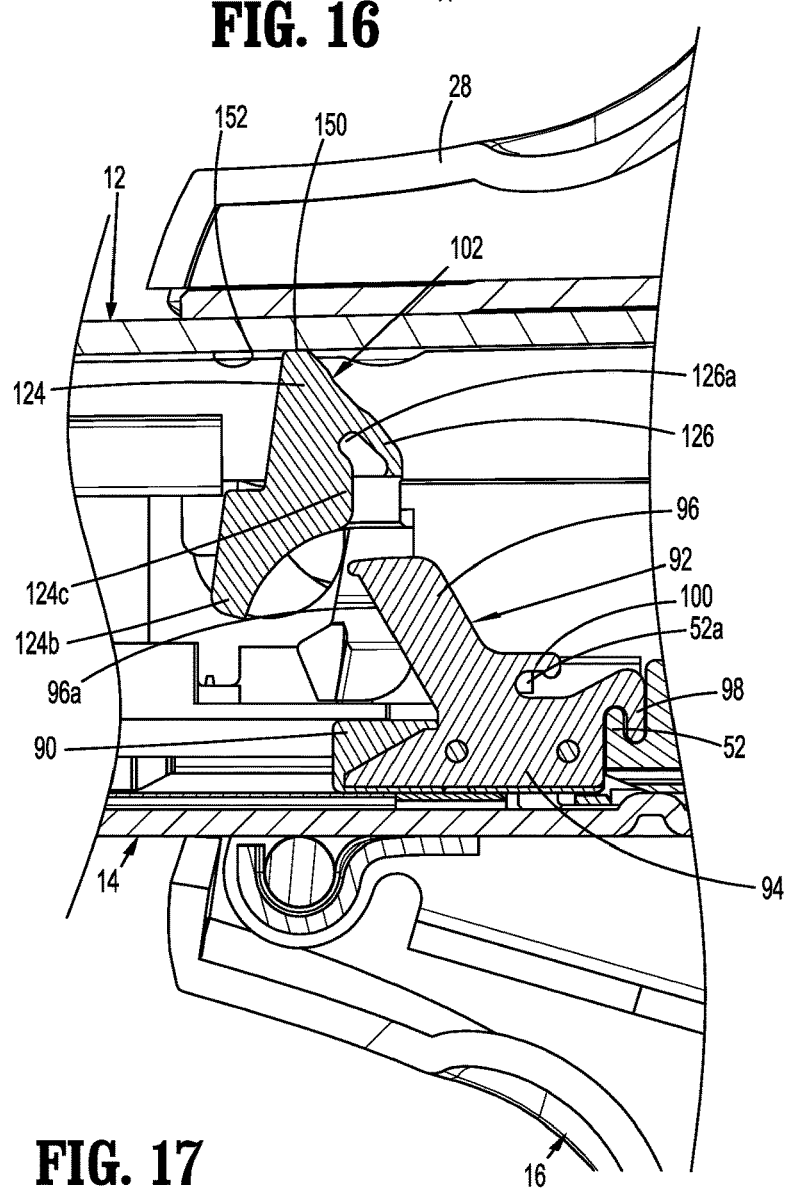
FIG. 17 is a cross-sectional view taken along section line 17-17 of FIG. 16.

FIGS. 16-18 illustrate the stapling device 10 as the anvil section 12 is attempted to be coupled to a cartridge section 14 having a spent or fired staple cartridge 18. As described above, after the anvil section 12 is separated from the cartridge section 14 and the lockout member 102 is pivoted to the locked position, the proximal portion 124a of the lockout member 102 projects upwardly from the cartridge body 66 of the staple cartridge 18. When an anvil section 12 is coupled to a cartridge section 14 having a spent staple cartridge 18, the proximal portion of the blocking member 110 of the locking member 102 is received between the spaced beams 12a and 12b of the anvil section 12 (FIG. 18) and the engagement surfaces 119a of the support blocks 119 of the lockout member 102 engage the beams 12a and 12b to prevent reclamping of the stapling device 10. In some aspects of the disclosure, the proximal portion 124a of the blocking member 110 of the lockout member 102 defines an abutment surface 150 that engages an inner surface 152 (FIG. 17) of the anvil section 12 to assist in preventing approximation of the anvil section 12 with the cartridge section 14.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly, shown and described, except as indicated by the appended claims.

What is claimed is:

1. A stapling device comprising:
    an anvil section having a proximal portion, a distal portion, and spaced beams, the proximal portion of the anvil section including a hand grip, and the distal portion of the anvil section including an anvil plate supported on the spaced beams;
    a cartridge section including a channel member defining a channel, the channel including a proximal portion and a distal portion, the channel member adapted to be coupled to the anvil section to facilitate movement of the anvil section in relation to the cartridge section between open and clamped positions;
    a firing assembly supported within the proximal portion of the channel and including a drive beam and a trigger;
    a clamp member supported on the cartridge section and movable from unclamped position to a clamped position to move the anvil section in relation to the cartridge section from the open position to the clamped position; and
    a staple cartridge releasably supported within the distal portion of the channel of the channel member of the cartridge section, the staple cartridge including a cartridge body, staples, pushers, an actuation sled, a knife assembly, and a lockout assembly, the cartridge body having a proximal portion and a distal portion and defining a central knife slot and staple receiving pockets positioned on opposite sides of the central knife slot, each of the staple receiving pockets receiving one of the staples and one of the pushers, the actuation sled positioned within the proximal portion of the cartridge body and being movable through the cartridge body into engagement with the pushers to eject the staples from the staple receiving pockets, the knife assembly including a knife bar having a cutting member, the cutting member including a member body having a distal edge and a cutting blade formed on the distal edge of the member body, the cutting blade positioned within the central knife slot and having an exposed portion extending above the cartridge body, the lockout assembly including a lockout member pivotably coupled to the proximal portion of the cartridge body and movable from an unlocked position to a locked position, the lockout member having a base portion that defines a knife slot and includes a blade guard positioned on each side of the knife slot of the base portion, the knife slot of the base portion of the lockout member receives the drive beam of the firing assembly, the blade guards positioned and configured to shield the exposed portion of the cutting blade when the lockout member is in the unlocked position while leaving the member body of the cutting member exposed, wherein in the locked position, the lockout member obstructs movement of the anvil section in relation to the cartridge section from the open position to the clamped position.

2. The stapling device of claim 1, further including a biasing member positioned to urge the lockout member towards the locked position.

3. The stapling device of claim 2, wherein the lockout member includes a blocking portion having a support block formed on each side of the knife slot of the base portion, each of the support blocks having an engagement surface that is positioned to engage one of the spaced beams of the anvil section when the lockout member is in the locked position to prevent movement of the anvil section in relation to the cartridge section from the open position to the clamped position.

4. The stapling device of claim 3, wherein the blocking portion has a distal portion that is positioned over but spaced from the knife bar when the lockout member is in the unlocked position and is positioned distally of the knife bar when the lockout member is in the locked position.

5. The stapling device of claim 4, wherein the distal portion of the blocking portion of the lockout member has an arcuate inner surface that faces the knife bar and a linear outer surface, the arcuate inner surface defining a central ridge and angled walls that are sloped outwardly from the central ridge.

6. The stapling device of claim 2, wherein the base portion of the lockout member includes pivot members that are coupled to the cartridge body to pivotably couple the lockout member to the cartridge body.

7. The stapling device of claim 6, wherein the biasing member includes a torsion spring that is positioned about one of the pivot members.

8. The stapling device of claim 1, wherein the knife assembly includes a support member that supports the knife bar, the support member positioned within the cartridge body proximally of the actuation sled and being movable into engagement with the actuation sled to advance the actuation sled through the cartridge body.

9. The stapling device of claim 1, wherein the knife bar includes a hook member that is configured to be coupled to the drive beam of the firing assembly when the staple cartridge is positioned within the channel of the channel member.

10. The stapling device of claim 1, wherein the knife bar includes a retainer that engages the lockout member when the lockout member is in the unlocked position to retain the lockout member in the unlocked position.

11. A staple cartridge comprising:
    a cartridge body configured for receipt within a cartridge section of a surgical stapler, the cartridge body having a proximal portion and a distal portion and defining a central knife slot and staple receiving pockets positioned on opposite sides of the central knife slot,
    a staple received within each of the staple receiving pockets of the cartridge body;
    a pusher received within each of the staple receiving pockets of the cartridge body, each of the pushers supporting one of the staples;
    an actuation sled positioned within the proximal portion of the cartridge body, the actuation sled movable through the cartridge body into engagement with the pushers to eject the staples from the staple receiving pockets;

a knife assembly including a knife bar having a cutting member, the cutting member including a member body having a distal edge and a cutting blade formed on the distal edge of the member body, the cutting blade positioned within the knife slot and having an exposed portion extending above the cartridge body; and a lockout assembly including a lockout member pivotably coupled to the proximal portion of the cartridge body and movable from an unlocked position to a locked position, the lockout member having a base portion that defines a knife slot and includes a blade guard positioned on each side of the knife slot, the blade guards positioned and configured to shield the exposed portion of the cutting blade when the lockout member is in the unlocked position while leaving the member body of the cutting member exposed, wherein in the locked position, the lockout member is configured to obstruct movement of the cartridge section, relative to an anvil section, from an open position to a clamped position.

12. The staple cartridge of claim 11, further including a biasing member positioned to urge the lockout member towards the locked position.

13. The staple cartridge of claim 12, wherein the lockout member includes a blocking portion having a support block formed on each side of the knife slot of the base portion, each of the support blocks having an engagement surface that is positioned to engage an anvil section of a stapling device when the lockout member is in the locked position.

14. The staple cartridge of claim 13, wherein the blocking portion has a distal portion that is positioned over but spaced from the knife bar when the lockout member is in the unlocked position and is positioned distally of the knife bar when the lockout member is in the locked position.

15. The staple cartridge of claim 14, wherein the distal portion of the blocking portion of the lockout member has an arcuate inner surface that faces the knife bar and a linear outer surface, the arcuate inner surface defining a central ridge and angled walls that are sloped outwardly from the central ridge.

16. The staple cartridge of claim 12, wherein the base portion of the lockout member includes pivot members that are coupled to the cartridge body to pivotably couple the lockout member to the cartridge body.

17. The staple cartridge of claim 16, wherein the biasing member includes a torsion spring that is positioned about one of the pivot members.

18. The staple cartridge of claim 11, wherein the knife assembly includes a support member that supports the knife bar, the support member positioned within the cartridge body proximally of the actuation sled and movable into engagement with the actuation sled to advance the actuation sled through the cartridge body.

19. The staple cartridge of claim 11, wherein the knife bar includes a proximally extending hook member.

20. A staple cartridge comprising:

a cartridge body having a proximal portion and a distal portion and defining a central knife slot and staple receiving pockets positioned on opposite sides of the central knife slot, a staple received within each of the staple receiving pockets of the cartridge body;

a pusher received within each of the staple receiving pockets of the cartridge body, each of the pushers supporting one of the staples;

an actuation sled positioned within the proximal portion of the cartridge body, the actuation sled movable through the cartridge body into engagement with the pushers to eject the staples from the staple receiving pockets;

a knife assembly including a knife bar having a cutting member, the cutting member including a member body having a distal edge and a cutting blade formed on the distal edge of the member body, the cutting blade positioned within the knife slot and having an exposed portion extending above the cartridge body; and a lockout assembly including a lockout member pivotably coupled to the proximal portion of the cartridge body and movable from an unlocked position to a locked position, the lockout member having a base portion and a blocking portion, the blocking portion having a distal portion, the base portion defining a knife slot, the distal portion positioned over but spaced from the knife bar when the lockout member is in the unlocked position and positioned distally of the knife bar when the lockout member is in the locked position, the distal portion of the blocking portion of the lockout member having an arcuate inner surface that faces the knife bar, the arcuate inner surface defining a central ridge and angled walls that extend outwardly from the central ridge.

\* \* \* \* \*